(12) United States Patent
Berkes et al.

(10) Patent No.: US 9,717,765 B2
(45) Date of Patent: *Aug. 1, 2017

(54) METHOD OF IDENTIFYING A BIOLOGICALLY-ACTIVE COMPOSITION FROM A BIOFILM

(71) Applicant: Quorum Innovations, LLC, Sarasota, FL (US)

(72) Inventors: Eva A. Berkes, Sarasota, FL (US); Nicholas T. Monsul, Sarasota, FL (US); Frederick T. Boehm, Sarasota, FL (US)

(73) Assignee: QUORUM INNOVATIONS, LLC, Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/349,371

(22) Filed: Nov. 11, 2016

(65) Prior Publication Data
US 2017/0056454 A1 Mar. 2, 2017

Related U.S. Application Data

(63) Continuation of application No. 13/503,325, filed as application No. PCT/US2011/059370 on Nov. 4, 2011, now Pat. No. 9,504,739.

(60) Provisional application No. 61/447,735, filed on Mar. 1, 2011.

(51) Int. Cl.

| | | |
|---|---|---|
| *G01N 33/00* | (2006.01) |
| *A61K 35/74* | (2015.01) |
| *A61K 35/644* | (2015.01) |
| *A61K 35/744* | (2015.01) |
| *A61K 8/67* | (2006.01) |
| *A61Q 11/00* | (2006.01) |
| *A61Q 17/00* | (2006.01) |
| *A61K 8/97* | (2017.01) |
| *A61K 8/98* | (2006.01) |
| *A61K 8/99* | (2017.01) |
| *A01N 63/02* | (2006.01) |
| *A61K 39/09* | (2006.01) |
| *A61K 45/06* | (2006.01) |
| *A61K 9/00* | (2006.01) |
| *A61K 35/747* | (2015.01) |
| *A61Q 19/10* | (2006.01) |
| *C12N 1/20* | (2006.01) |
| *C12Q 1/04* | (2006.01) |
| *A61K 36/61* | (2006.01) |

(52) U.S. Cl.
CPC ............ *A61K 35/74* (2013.01); *A01N 63/02* (2013.01); *A61K 8/67* (2013.01); *A61K 8/97* (2013.01); *A61K 8/981* (2013.01); *A61K 8/988* (2013.01); *A61K 8/99* (2013.01); *A61K 9/007* (2013.01); *A61K 9/0043* (2013.01); *A61K 9/0046* (2013.01); *A61K 9/0048* (2013.01); *A61K 35/644* (2013.01); *A61K 35/744* (2013.01); *A61K 35/747* (2013.01); *A61K 39/092* (2013.01); *A61K 45/06* (2013.01); *A61Q 11/00* (2013.01); *A61Q 17/005* (2013.01); *A61Q 19/10* (2013.01); *C12N 1/20* (2013.01); *C12Q 1/04* (2013.01); *A61K 36/61* (2013.01); *A61K 2300/00* (2013.01); *A61K 2800/78* (2013.01); *A61K 2800/782* (2013.01); *G01N 2333/315* (2013.01); *G01N 2333/335* (2013.01)

(58) Field of Classification Search
CPC ....................................................... A61K 35/74
See application file for complete search history.

(56) References Cited

U.S. PATENT DOCUMENTS

| | | |
|---|---|---|
| 5,049,492 A | 9/1991 | Sauer et al. |
| 5,352,586 A | 10/1994 | Dobrogosz et al. |
| 5,439,678 A | 8/1995 | Dobrogosz et al. |
| 6,051,552 A | 4/2000 | Reid et al. |
| 6,184,027 B1 | 2/2001 | Laine et al. |
| 6,479,051 B1 | 11/2002 | Bruce et al. |
| 7,491,386 B2 | 2/2009 | Comelli et al. |
| 7,794,726 B2 | 9/2010 | Levine |
| 8,691,538 B1 | 4/2014 | Moll et al. |
| 8,741,855 B2 | 6/2014 | Quave et al. |
| 8,906,393 B2 | 12/2014 | Kaplan et al. |

(Continued)

FOREIGN PATENT DOCUMENTS

| | | |
|---|---|---|
| JP | 2002-522464 | 7/2002 |
| JP | 2003-534362 | 11/2003 |

(Continued)

OTHER PUBLICATIONS

Ahimou, F. et al., "Surfactin and iturin A effects on Bacillus subtilis surface hydrophobicity." *Enzyme Microb. Technology*, 2000, 27: Abstract.

(Continued)

*Primary Examiner* — Albert Navarro
(74) *Attorney, Agent, or Firm* — Saliwanchik, Lloyd & Eisenschenk

(57) ABSTRACT

The subject invention provides materials and methods that effectively support innate immunity and/or disperse pathogenic biofilms using readily available, nontoxic, natural substances, while supporting restoration of normal microbiotic homeostasis. In one embodiment, the subject invention provides anti-biofilm compositions comprising one or more probiotic organisms, anti-microbial honey, and other ingredients such as prebiotic compounds, other hive products, green tea derivatives, other plant derivatives, and vitamin D3.

20 Claims, No Drawings

(56) References Cited

U.S. PATENT DOCUMENTS

| | | | |
|---|---|---|---|
| 9,504,739 | B2* | 11/2016 | Berkes .............. A61K 35/644 |
| 2002/0123077 | A1 | 9/2002 | O'Toole et al. |
| 2002/0160444 | A1 | 10/2002 | Reynolds et al. |
| 2003/0103912 | A1 | 6/2003 | Levin et al. |
| 2003/0171421 | A1 | 9/2003 | Davies et al. |
| 2003/0215433 | A1 | 11/2003 | Kokai-Kun et al. |
| 2003/0235559 | A1 | 12/2003 | Sobol et al. |
| 2004/0076614 | A1 | 4/2004 | Schur |
| 2004/0132095 | A1 | 7/2004 | Iizumi et al. |
| 2005/0074442 | A1 | 4/2005 | Ranganathan |
| 2005/0287573 | A1 | 12/2005 | Stafslien et al. |
| 2006/0073129 | A1 | 4/2006 | Doyle et al. |
| 2006/0263344 | A1 | 11/2006 | Skop et al. |
| 2007/0036776 | A1 | 2/2007 | Reid et al. |
| 2007/0059295 | A1 | 3/2007 | Wang et al. |
| 2007/0098745 | A1 | 5/2007 | Bruno |
| 2007/0110680 | A1 | 5/2007 | Davies et al. |
| 2007/0207095 | A1 | 9/2007 | Davies |
| 2008/0169238 | A1 | 7/2008 | Jesus Simoes Campos Tavares et al. |
| 2009/0017514 | A1 | 1/2009 | Datta et al. |
| 2009/0155296 | A1 | 6/2009 | Levine |
| 2009/0258404 | A1 | 10/2009 | Mikkelsen et al. |
| 2010/0086528 | A1 | 4/2010 | Olofsson et al. |
| 2010/0159555 | A1 | 6/2010 | Leukes et al. |
| 2012/0225098 | A1 | 9/2012 | Kaplan et al. |
| 2013/0336942 | A1 | 12/2013 | Leser et al. |
| 2014/0030750 | A1 | 1/2014 | Decho et al. |

FOREIGN PATENT DOCUMENTS

| | | |
|---|---|---|
| JP | 2005-500267 | 1/2005 |
| WO | WO 00/09080 | 2/2000 |
| WO | WO 01/30806 A1 | 5/2001 |
| WO | WO 01/91711 A1 | 12/2001 |
| WO | WO 02/31184 A2 | 4/2002 |
| WO | WO 03/070919 A1 | 8/2003 |
| WO | WO 2005/111080 | 11/2005 |
| WO | WO 2007/137369 A1 | 12/2007 |
| WO | WO 2008/043175 A1 | 4/2008 |
| WO | WO 2009/100456 A2 | 8/2009 |

OTHER PUBLICATIONS

Allaker, R.P. and Douglas, C.W.I., "Novel Anti-Microbial Therapies for Dental Plaque-Related Diseases," *International Journal of Antimicrobial Agents*, 2009, vol. 33, pp. 8-13.

Annous, B.A. et al., "Quorum Sensing in Biofilms: Why Bacteria Behave the way they do." *Journal of Food Science*, 2009, 74(1): R24-R37.

Azeredo, J. et al., "Methods of extract the exopolymeric matrix from biofilms: A comparative Study." *Centre of International Research for Water and Environment*, 1999, 333-340.

Bruhn, Jesper B. et al., "Ecology, Inhibitory Activity and Morphogenesis of a Marine Antagonistic Bacterium Belonging to the Roseobacter Clade." *Applied and Environmental Microbiology*, Nov. 2005, 7263-7270.

Database WPI, "Yogurt Composition Having Reducing and Proliferation-Inhibiting Action of Helicobacter Pylori Infectious Bacteria in Stomach," Accession No. 2003-154343, Sep. 16, 2002.

De Araujo, C. et al., "Quorum sensing affects biofilm formation through lipopolysaccharide synthesis in Klebsiella pneumoniae." *Research in Microbiology xx*, Jun. 2010, 1-10.

Jones, Sara E. et al., "Probiotic Lactobacillus reuteri biofilms produce antimicrobial and anti-inflammatory factors." *BMC Microbiology*, 2009, 9(35): 1-9.

Kanmani, Paulraj et al., "Production and purification of a novel exopolysaccharide from lactic acid bacteria Streptococcus phocae P189 and its functional characteristics activity in vitro," *Bioresource Technology*, 2011, 102: 4827-4833.

Kehl-Fie, Thomas E. et al., "Examination of Type IV Pilus Expression and Pilus-Associated Phenotypes in Kingella kingae Clinical isolates." *Infection and Immunity*, Apr. 2010, 78(4): 1692-1699.

Kim, Y. et al., "Released exopolysaccharide (r-EPS) produced from probiotic bacteria reduce biofilm formation of enterohemorrhagic *Escherichia coli*." *Biochemical and Biophysical Research Communications*, 2009, 379: 324-329.

Kleerebezem, Michiel et al., "Peptide pheromone-dependent regulation of antimicrobial peptide production in Gram-positive bacteria: a case of multicellular behavior." *Peptides*, 2001, 22: 1579-1596.

Kwan, J.C. et al., "Lyngbyoic acid, a "Tagged" fatty acid from a marine cyanobacterium, disrupts quorum sensing in Pseudomonas aeruginosa." *Molecular Biosystems*, Apr. 2011, 7(4): 1205-1216, supplemental material pp. 1-17.

Lakhtin, M. et al., "Probiotic Lactobacillus and Bifidobacterial Lectins Against Candida albicans and Staphylococcus aureus Clinical Strain: New Class of the Pthogen Biofilm Destructors." *Probiotic and Antimicro. Prot.*, Aug. 2010, 2: 186-196.

Lepargneur, J.P., "Role protecteur de la flore de Doderlein." *Journal of Gynecology, Obstetrics and Biological Reproduction*, 2002, 31: Abstract.

Leriche, V. et al., "Behaviour of L. monocytogenes in an artificially made biofilm of a nisin-producing strain of Lactococcus lactis." *International Journal of Food Microbiology*, Oct. 1999, 51(2-3): 169-182.

Lin, Yi-Han et al., "Acyl-homoserine lactone acylase from Ralstonia strain Xj12B represents a novel and potent class of quorum-quenching enzymes." *Molecular Microbiology*, 2003, 47(3): 849-860.

McLean, Robert J. C. et al., "Evidence of autoinducer activity in naturally occurring biofilms." *FEMS Microbiology Letters*, Sep. 1997, 154: 259-263, doi: http://dx.doi.org/10.1111/j.1574-6968.1997.tb12653.x 259-263.

Merritt, Justin et al., "Mutation of luxS Affects Biofilm Formation in *Streptococcus mutans*." *Infection and Immunity*, Apr. 2003, 71(4): 1972-1979.

Muller, Henry et al., "Quorum-sensing effects in the antagonistic rhizosphere bacterium Serratia plymuthica HRO-C48." *FEMS Microbiological Letters*, 2009, 67: 468-478.

Sanchez, B. et al., "Extracellular proteins secreted by probiotic bacteria as mediators of effects that promote mucosa bacteria interactions." *Microbiology*, Nov. 2010, 156(11): 3232-3242.

Singh, Pooja et al., "Potential applications of microbial surfactants in biomedical sciences." *Trends in Biotechnology*, Mar. 2004, 22(3): 142-146.

Stickler, David J. et al., "Biofilms on Indwelling Urethral Catheters Produce Quorum Sensing Signal Molecules In Situ and In Vitro." *Applied and Environmental Microbiology*, Sep. 1998, 64(9): 348603490.

Taechowisan, T. et al., "*Streptomyces* sp. ST8 extracts attenuate growth, scid production, adhesion, biofilm formation, and water-insoluble glucan synthesis of *Streptococcus mutans*." *Microbial Ecology in Health and Disease*, 2009, 21: 78-86.

Talarico, T.L. et al., "Chemical characterization of an antimicrobial substance produced by Lactobacillus reuteri." *Antimicrobial Agents and Chemotherapy*, 1989, 33(5): 674-679.

Van Der Mei, Henny C. Ph.D. et al., "Comparison of the microbial compositions of voice prosthesis biofilms from patients requiring frequent versus infrequent replacement." *Ann. Otol. Rhinol. Laryngol.*, 2002, 111: 200-203.

Van Houdt, R. et al., "Biofilm formation and cell to cell signaling in Gram Negative bacteria isolated from a food processing environment." *Journal of Applied Microbiology*, 2004, 96: 177-184.

Van Houdt, Rob et al., "Genotypic and phenotypic characterization of a biofilm-forming Serratia plymuthica isolate from a raw vegetable processing line." *Microbiological Letters*, 2005, 246: 265-272.

You, JianLan et al., "Inhibition of Vibrioi biofilm formation by a marine actinomycete strain A66." *Applied Microbiology and Biotechnology*, 2007, 76: 1137-1144.

(56) References Cited

OTHER PUBLICATIONS

Zhang, X et al., "Comparison of extraction methos for quantifying extracellular polymers in biofilms." *Water Science and Technology*, 1999, 39(7): 211-218.

\* cited by examiner

METHOD OF IDENTIFYING A BIOLOGICALLY-ACTIVE COMPOSITION FROM A BIOFILM

CROSS-REFERENCE TO A RELATED APPLICATION

This application is a continuation of U.S. application Ser. No. 13/503,325, filed May 31, 2012; now U.S. Patent No. 9,504,739; which is a National Stage Application of International Application Number PCT/US2011/059370; filed Nov. 4, 2011; which claims the benefit of U.S. provisional application Ser. No. 61/447,735, filed Mar. 1, 2011, all of which are incorporated herein by reference in their entirety.

BACKGROUND OF THE INVENTION

In a world where only the fittest survive, bacteria have a remarkable capacity to adapt and evolve in response to their environment. Some microbes have evolved a critical survival advantage through their symbiotic relationship with their host. In exchange for a convenient growth "niche" in and on their human hosts, these bacteria confer certain important survival advantages, such as direct inhibition of pathogen colonization on the surfaces where these "friendly" bacteria thrive. Under ordinary circumstances the human immune system would have fought off these self-same bacteria as hostile invaders. But by conferring certain health benefits upon their human hosts, these "probiotic" bacteria create a beneficially synergistic, evolutionarily advantaged and thus evolutionarily conserved relationship between microbe and man.

Among the benefits conferred by probiotic organisms is stimulation of the host innate immune system. As the main and first defender against all infections, the integrity, efficiency and rapidity of the innate immune system response is critical for host survival. An intact and smoothly functioning innate immune system protects the host as well as its probiotic organisms by limiting host pathogen colonization. While beneficial to the host, such protection is also self-serving to the probiotic organism, since direct inhibition of pathogen growth conversely also promotes the growth of healthy, beneficial organisms on these same surfaces. Therefore, these benefits just as importantly protect the microbiota conferring this advantage while simultaneously protecting the host itself. Most microbes, however, are not probiotic, but are at best, nonpathogenic, and at worst, possibly lethal.

The century-old germ theory—that only one free-floating "germ" or microbe is needed to confer infection—directly shaped the subsequent study of pathogens and their resulting infections. Antibiotics, which are the main tools in treating infections, are based on the efficiency of microbial killing of microbes studied in free-floating (planktonic) state, functioning as a single cell. Quantification of antibiotic efficacy is done in traditional Minimum Inhibitory Concentration (MIC) assays. Traditional microbiology has been wrong, however. To the contrary, most human infections are now understood to be due to the coordinated, en masse behavior of entire microbial colonies. These colonies are composed of microbes working together to secrete an extracellular matrix called biofilm which surrounds and protects the entire colony from antibiotics and attack by an intact immune system.

Biofilms are initiated when free-floating, planktonic bacteria anchor to biologic or inert surfaces such as indwelling medical devices. The attached bacteria multiply and progress from a state of monolayer to a microcolony and then to a critical mass, at which bacterial crosstalk occurs, triggering a phenomenon known as quorum sensing that leads to the biofilm phenotype. Quorum sensing turns on biofilm-producing genes not expressed or produced in non-sessile bacteria. The bacteria respond collectively to express factors that are specific to the biofilm phenotype, which lead to the secretion of an exopolysaccharide (EPS) matrix definitive of biofilm. This biofilm phenotype is characterized morphologically by the formation of microbial towers, which are composed of layers of embedded, live bacteria with intervening water channels. Under the right environmental conditions, free-floating bacteria are released from the biofilms, and the cycle is continued at other surfaces.

Approximately 80% of the world's microbial biomass resides in the biofilm state, and the National Institutes of Health estimates that more than 75% of microbial infections that occur in the human body are underpinned by the formation and persistence of biofilms. Such infections include dental caries, periodontitis, musculoskeletal infections, osteomyelitis, bacterial prostatitis, endocarditis, chronic bronchitis and other states of chronic lower respiratory inflammation, cystic fibrosis pneumonia, otitis media, chronic tonsillitis, adenoiditis and device infections.

Although it might seem that biofilms are "just another type of infection", pathogenic biofilms behave completely differently than the very same bacteria in free-floating, non-biofilm producing form. Due to completely different genomic expression, biofilm related infections have a different clinical course and antibiotic response than planktonic-type infections. Moreover, treating biofilm associated infections "the same" as planktonic infections creates antibiotic-resistant "superbugs" because the EPS matrix generated by the colony gives the colony 1000-fold resistance against antibiotics which would ordinarily kill these microbes if in free-floating form.

Because antibiotics fail to eradicate these EPS-protected microbial communities, use of antibiotics actually compounds the problem because antibiotics select for and perpetuate increasingly antibiotic-resistant bacteria. These "super bugs" include methicillin resistant *Staphylococcus aureus* (MRSA), the world's leading cause of nosocomial infection, and a bacterium now widespread in the community at large. Despite the global ramifications of inadvertent "super bug" creation, modern medicine has few treatments for pathogenic biofilm associated infections. Furthermore, the solution to this problem is not merely the development of another new antibiotic, because in order to avoid perpetuation of antibiotic-resistant "super bugs", such treatments must have broad-spectrum as well as anti-biofilm activity. This is reflected time and time again in real patients, for whom even repeat, extended courses of antibiotics "proven" effective in MIC tests are often unsuccessful.

Attacking, dissolving or otherwise weakening the bacterial biofilm matrix, interrupting the quorum mechanisms maintaining the bacterial community, as well as upregulating local host innate immunity could cure what would otherwise become incurable chronic infection or chronic biofilm-associated inflammatory disease. Penetration or dispersion of the bacterial biofilm "armor" is critical in fighting biofilm-induced chronic inflammation, particularly those involving "super bugs".

In vitro antibiotic efficacy test results can dramatically underestimate the protection conferred by pathogenic biofilms in vivo against the tested and supposedly effective antibiotic. Due to biofilm's protective properties, antibiotic choices based on these results may be irrelevant, misleading and even clinically harmful. Indeed, even repeat, extended courses of antibiotics demonstrated in MIC studies as effective are often unsuccessful in patients afflicted with biofilm-associated inflammatory states.

Not only are bacteria in biofilm state robustly resistant to antibiotics, they are also resistant to other anti-bacterials and biocides, such as alcohols, acids and iodine solutions. In fact, today's "antiseptics" such as popular hand "sanitizers" may be part of the problem, since use of such biocides may actually increase the prevalence of pathologic biofilms on involved surfaces, such as the hands of healthcare workers. Therefore, developing non-antibiotic methods of inducing biofilm dissociation and/or prevention of biofilm secretion is an area of increasing research.

Not all biofilm is pathogenic, however. Gastrointestinal probiotics secrete biofilm that protects the mucosal surface against intestinal infection by pathogenic biofilm-forming organisms. Additionally, synergistic probiotics, such as certain species of *Lactobacillus* and *E. coli*, give the host other benefits, such as normal intestinal motility, toxin elimination and the efficient absorption of nutrients such as vitamin B12. Moreover, from an evolutionary perspective, the human body requires colonization by probiotic microbes for survival advantage. This mutual interdependence exemplifies the synergistic relationship between human host and its beneficial microbiota.

The human host mounts an inflammatory reaction as a normal response to pathogen invasion and accompanying biofilm formation. If such an inflammatory reaction is sustained, this inappropriate over-stimulation of an initially normal immune response can result in damage to and disease of the human host itself. However, probiotic organisms, unlike their pathogenic counterparts, maintain a healthy and balanced immune response. In other words, probiotics maintain homeostasis between host inflammatory and anti-inflammatory reactions.

Inflammation is a complex phenomenon, involving recruitment of white blood cells, leakage of fluid from capillaries as well as release of chemical mediators and oxidants necessary to kill invading microbes. Maintaining immune homeostasis is important because host-produced inflammation can cause damage to the host itself. These very same processes, if not "switched off" once eradication of pathogens has occurred, result in local tissue damage, bodily harm and consequent disease.

Probiotic organisms upregulate the body's immune surveillance against pathogens but also down-regulate inflammatory signals. This constant balancing act by probiotics helps to maintain the delicate but critical homeostasis between immune stimulation and immune over-stimulation. Disruption of this homeostasis can result in certain common human diseases with a common unifier of chronic inflammatory state such as meibomian gland dysfunction and chronic rhinosinusitis.

Biofilms have broad-ranging clinical relevance in all areas of medicine. Bacterial biofilms such as those commonly associated with *Pseudomonas* and *Staphylococcus* are known to be a cause of intractable infection as well as chronic low-grade inflammation. They consist of colonies of bacterial organisms that collectively secrete and form a protective layer of extracellular matrix material. The bacterial colonies in bacterial biofilms appear to be very resistant to the hosts' natural defenses as well as antibiotic treatments. Biofilms colonize virtually any surface in or on the human body to which these colonies can adhere. They often colonize biomaterials such as urinary catheters, transcutaneous intravenous lines and prosthetic heart valves.

Dry eye is a medical condition that affects >10 million people in the United States alone. It is arguably the most common ophthalmic condition. Its frequency in general ophthalmology practices can be as high as 50%. It results from the deficiency in the production and/or composition of tears produced by the eye's lacrimal and adnexal secretory glands. The eye depends on the constant flow of tears to lubricate the surface of the eye, maintaining vision and overall comfort of the eyes. Tears are composed of water, oils, mucus, antibodies and other proteins. These are all normally secreted by the lacrimal gland located around the eyes and the meibomian glands of the eye lids. When there is an imbalance in the amount of tears and/or abnormalities in the composition and/or amount of the tear constituents, a person may experience many different symptoms of dry eye—blurring of the vision, eye irritation, redness, itching, pain and sensation of ocular "foreign body".

The vast majority of dry eye conditions are due to meibomian gland dysfunction, associated with ocular rosacea, blepharitis and ocular allergy. Repercussions of dry eye syndrome include significant negative impact on quality of life, corneal damage, ongoing ocular and periocular inflammation and even infection. Common symptoms of dry eye syndrome include dry, scratchy, sandy or gritty feeling, foreign body sensation, pain or soreness, stinging, burning, eye fatigue, itch, increased blink frequency, photophobia, blurry vision, redness, mucus discharge, intolerance of contact lens wear and even excessive tearing. These symptoms can be due to many conditions, including lupus, rheumatoid arthritis, Sjogren's syndrome, normal aging, contact lens use, any corneal surgery such as LASIK, diabetes, meibomian gland dysfunction of any cause, anatomic abnormality, extended computer use, and medications, as well as other common ocular surface disorders such as allergic conjunctivitis. Increased leukocytes and cytokine mediators are found on the ocular surface of the dry eye, indicating ongoing inflammation.

Lid and ocular hygiene methods are commonly recommended in an attempt to dilute and remove local irritants and inflammatory chemicals thought to be influencing chronic ocular and periocular inflammation. The most common recommendations include dilute baby shampoo lid scrubs as well as other over-the-counter cleansers. However, none of these products is sufficiently antibacterial to kill eyelid bacteria within clinically relevant exposure times.

Although dry eye syndrome has many causes, the pathology common to dry eye syndrome regardless of cause is abnormal change on the ocular surface due to alterations in quality or quantity of tears. Tear fluid consists of 3 layers—a hydrophilic mucus layer and aqueous and lipid layer. Adjacent to the cornea, the mucus layer is produced by conjunctival goblet cells and absorbed by corneal surface glycoproteins. Despite potentially normal quantity of tear production, deficiency or dysfunction of the mucin itself can lead to poor wetting and/or glycation of the corneal surface, and thus desiccation and epithelial damage common in dry eye syndrome. Forming the majority of tear volume, the aqueous layer is secreted by the lacrimal glands and is adjacent to the mucus layer. The high volume and diffusability of the aqueous component delivers nutrients and oxygen to the cornea, which does not otherwise itself receive a great amount of blood and nutrient flow. The final layer is the lipid layer, secreted by the meibomian, Zeiss and Moll glands of the lids. Lipids in this layer function as surfactants and emollients by lowering the surface tension of the aqueous fluid, allowing efficient dispersal of tear fluid over the ocular surface, and slowing evaporation of the aqueous layer of tears. Because the lacrimal and meibomian glands have androgen receptors, low androgen status can result in abnormality of the lipid layer, hastening tear evaporation and resulting in dry eyes.

Dry eye syndrome can further be characterized by the component of tear fluid most affected. Therefore, dry eye syndrome can be divided into lubricant deficiency dry eye, aqueous tear deficient dry eye and evaporative dry eye. Lubricant deficiency dry eye involves abnormality of the tear mucin layer. The mucin layer can be disrupted by a number of conditions, including allergic conjunctivitis, direct chemical irritation (such as preservatives in ocular drops), volatile mucosal irritants, viral infection, thermal damage, and nutritional/metabolic disorders such as vitamin deficiency and protein malnutrition.

Aqueous tear deficient dry eye is due to abnormal function or amount of the aqueous layer secreted by the lacrimal gland. Tear deficiency can result from many systemic conditions, such as Sjogren's syndrome, Sjogren's disease, lupus, rheumatoid arthritis, and diabetes, as well as the normal aging process associated with lacrimal gland atrophy. Other causes include ocular chemical irritants, lacrimal gland damage, viral infection, menopause and medications such as diuretics, antihistamines, oral contraceptives or hormone therapy, anti hypertensives, antidepressants and systemic vasoconstrictors.

Evaporative dry eye is due to abnormality of the lipid layer. Because the lipid layer is unable to function as an effective surfactant and emollient, it causes excessive evaporation of the tear fluid layer. Most commonly, evaporative dry eye is due to meibomian gland dysfunction, environmental conditions (airborne irritants, low ambient humidity, high ambient temperature) and computer use, which markedly lowers normal blink frequency, causing more rapid evaporation of tear fluid from the corneal surface.

In addition to abnormality of the tear fluid layers, there are other causes of dry eyes. These include anatomic (excessive exposure of surface of the eyes as in Grave's disease, eversion of eye lids associated with normal senescence) and neural causes. Neural stimulation of the ocular surface results normally in direct feedback to the lacrimal gland, which then adjusts secretion appropriately in response. This neural feedback is inhibited by peripheral nerve damage affecting ocular sensation, cerebrovascular accident or, more commonly, LASIK corneal surgery. Ocular and orbital surgery can cause dry eye syndrome simply due to the physical impact on the tissues with instrumentation and surgical trauma. Furthermore, abnormal proportions and/or amounts of essential fatty acids (EFA) such as linoleic acid and imbalance between omega-3 and omega-6 EFAs can lead to ocular surface inflammation and dry eyes. Extended use of contact lenses can cause dry eyes due to mechanical interference with normal distribution of nutrients and oxygen, as well as the chronic deposition of matter that typically occurs on contact lenses themselves. These micro-concretions become a nidus for bacterial growth and pathogenic biofilm production from *Pseudomonas* and *Staphylococcus* as well as a cause of ongoing micro- trauma to the corneal epithelium.

Regardless of the particular cause of ocular surface disturbance, chronic inflammation at the ocular surface is the end result. The innate immune system appears to be the predominant initiator of this process. In dry eye syndrome of any cause, low-level, ongoing ocular surface and peri-ocular infiltration of immune cells such as conjunctival CD4 T cells and corneal CD11b+ monocytes develops. Localized tissue stress induced by ocular surface dryness induces secretion of inflammatory cytokines such as IL-1, TNF-alpha and IL-6. These substances activate nearby antigen presenting cells (APCs), which in turn cause the expansion of Th17 cells producing IL-17 as well as Th1 cells producing IFN-gamma. The elaborated cytokines IL-17 and IFN-gamma perpetuate the inflammatory response by increasing leukocyte migration to the ocular surface. Over time, this low-level inflammation can make the eye more susceptible to bacterial, viral and other infections.

Although the high frequency of chronic dry eye syndrome in the general population establishes ongoing need, there are currently no particularly effective treatments for this condition. Over-the-counter treatments provide short-lived symptomatic relief and fail to address the underlying issue of ocular inflammation. Indeed, use of these products often aggravates dry eyes themselves. Ocular preservatives in artificial tears often worsen dry eye syndrome due to corneal damage resulting from prolonged exposure to these chemicals. Overuse of topical vasoconstrictors that "get the red out" also can exacerbate corneal inflammation. In the prescription drug category, in the past decade, only 1 new product going beyond the category of artificial tears has been approved in the United States for treatment of dry eyes—namely, Restasis (cyclosporine). Topical cyclosporine is very costly, and has a significant side effect profile, as well as a poor clinical response rate of only 15%. Therefore, relieving the symptoms of dry, irritated and/or inflamed eyes is currently limited to ocular fluid supplementation (i.e., use of artificial tears), surgical treatment via punctal plug to decrease tear fluid loss into the nasolacrimal duct, use of potentially hazardous pharmaceutical drugs or therapeutic ocular equipment such as "moisture chamber spectacles" and therapeutic contact lenses. However, these methods are costly, unwieldy, can further perpetuate ocular pathology and moreover are only partially effective.

Current drug development is focusing on several new pharmaceutical products. There is some evidence that topical hormonal therapy may help relieve chronic dry eyes. Also in the pipeline are a modified cyclosporine, topical steroidal and non-steroidal anti-inflammatories, oral a-3 adenosine receptor agonists, synthetic anti-inflammatory molecules known as resolvins, anti-LFA-1 compounds, proinflammatory interleukin antagonists, immunosuppressant monoclonal antibodies, topical antibiotics, chemical secretagogues and an artificial tear solution containing hyaluronic acid. However, all of these with the exception of the last are expensive pharmaceutical products, and the hyaluronic acid drops function similarly to artificial tears already on the market. Secondary treatment modalities have included topical antibiotic therapy to address the often low-grade infections associated with dry eyes. Despite the frequency of dry eyes, universally accepted treatment modalities are inadequate, as is evidenced by current extensive research and ongoing drug development in this area. Today's research efforts are focusing on development of synthetic immunomodulatory pharmaceuticals—no new over-the-counter ocular anti-inflammatory compound currently exists or is known to be planned.

*Lactobacillus* extracts have been previously used in cosmetic applications (U.S. patent application Ser. No. 11/70, 810, L'Oreal patent, WO9907332, JP 3112983, JP 2002037739). However, *Lactobacillus* has not previously been used in the treatment of dry eyes. Honey has also been used in cosmetic applications for the treatment of chronic skin inflammation and/or infection. However, honey has not previously been used in the treatment of dry eyes.

Prior to the subject invention, treatment of chronic sinusitis often involves pronged and repeated antibiotics, intranasal as well as systemic corticosteroids and even otolaryngologic surgery. However, even though chronic rhinosinusitis is increasingly recognized as a biofilm-related disease, no treatment exists which is directed at the biofilm component of the condition itself. The same kind of solutions proposed in this invention for dry eye syndrome can also be applied in the treatment of and symptom relief from chronic rhinosinusitis.

Like chronic sinusitis, chronic periodontitis is widespread in the general population. Along with genetic and environmental factors, dental plaque biofilm is necessary for the development of chronic periodontal disease. Even though there is inadequate evidence to establish causality at this time, many studies have shown a clear and parallel relationship between oral disease and atherogenesis in heart disease. Nevertheless, treatment of oral disease leads to both a reduction in the systemic inflammatory burden as reflected in inflammatory markers such as hsCRP and an improvement in endothelial function. Currently, however, the only treatments available for chronic gingival and periodontal disease are debridement and antibiotics taken systemically or applied subgingivally. However, as stated above, antibiotics are generally poorly effective against pathogenic biofilms.

Other widespread chronic inflammatory disorders involve the respiratory tract. These include allergic rhinoconjunctivitis, chronic bronchitis and asthma. Less common conditions such as cystic fibrosis and aspergillosis have clearly been established to involve biofilms such as *Pseudomonas* and *Aspergillus* biofilm, causing significant morbidity and mortality. Treatments in all of these conditions include steroids and systemic antibiotics and antifungals. In particular, sometimes macrolide antibiotics, which are antibiotics with immunomodulatory properties, may benefit patients with respiratory diseases associated with chronic inflammation, in part because they may decrease biofilm formation. However, there is no other non-invasive therapeutic option besides antimicrobials or steroids at this time.

Today's antibiotics clearly and repeatedly demonstrate profound failure to treat biofilm-associated infection. Moreover, there are no well known or proven anti-biofilm treatments per se. Attempts to treat infections presumed secondary to pathogenic biofilm formation include repeated and prolonged antibiotic therapy, physical removal of the biofilm (i.e., surgery or debridement) and topical sterilizers such as alcohol based foams or gels used for hand cleansing. Not only do these treatments fail to restore normal physiology, they disrupt the homeostasis of innate immunity—antibiotics breed increasingly resistant "super bugs", surgery or debridement results in anatomic wounding which creates another potential site for infection, and topical disinfectants may encourage development and growth of pathogenic biofilms by eradicating normal commensals as well as pathogens.

It is likely that current anti-infectives may be failing to treat many of the world's infections because such treatment fails to treat the biofilm component, and in fact, may even result in increased pathogenic biofilm growth and worsened infection. Moreover, formation and attachment of the biofilm itself may create the window of opportunity enabling that particular pathogen to cause infection. In order to be effective, treatments must be targeted against pathogen biofilm disruption, must support rather than disturb normal innate immunity and should interrupt quorum sensing mechanisms responsible for maintaining pathogenic biofilms.

In the ocular field, it would be very useful if it were possible to elicit anti-inflammatory and/or anti-biofilm effects directly on the ocular surface using safe, inexpensive and locally administered compounds, rather than antibiotics, synthetic immunomodulators or systemically delivered compounds. It would also be very useful to be able to further limit or even avoid the use of chemical preservatives present in most ocular drops, as these chemicals themselves can worsen ocular surface inflammation.

Presently, there is no method or treatment available for eliciting anti-inflammatory and anti-biofilm effects on the ocular surface of individuals with symptoms of dry eye syndrome, dry eyes and/or chronically inflamed, red or irritated eyes. Moreover, there is a profound lack of non-antibiotic, non-invasive anti-biofilm therapy which can potentially cure antibiotic-resistant "superbug" infections without perpetuating the global problem of antibiotic resistance. Furthermore, current treatments such as antibiotics or surgical intervention have significant associated side effects, cost, and treatment failure as well as repercussions on the rest of the body, including the "uninvolved" areas.

It would also be desirable for a treatment to be applied directly to the areas affected by pathogenic biofilms, including surfaces such as human mucosa and keratinized and non-keratinized epithelium. Such topical administration techniques would circumvent systemic toxicity, since they are by definition administered via localized (skin medicament, nasal spray, oral inhaler or nebulizer, ocular drop, oral troche, et cetera) delivery systems. Also desirable would be for treatments to be inexpensive and safe, for example, if treatments were to be comprised of natural, generally regarded as safe (GRAS) derivative/non-pharmaceutical ingredients. Lastly, it would be useful if anti-biofilm compounds could be applied to inert surfaces (i.e., hospital equipment, airplane tray tables, school desks) to limit the spread/presence of pathogenic biofilms in the hospital/clinical environment as well as in the community at large.

SUMMARY OF THE INVENTION

The subject invention provides materials and methods that effectively support innate immunity and/or disperse pathogenic biofilms using readily available, nontoxic, natural substances, while supporting restoration of normal microbiotic homeostasis.

The compositions of the subject invention can be delivered to the affected tissues by direct application, significantly increasing both efficacy and safety. Because the composition is applied directly to an area affected by a pathogenic biofilm, including surfaces such as human mucosa and keratinized and non-keratinized epithelium, it directly addresses the current need for non-invasive anti-biofilm treatments.

Examples of such locally directed therapies include skin medicaments, nasal sprays and washes, ear drops, oral inhalers and nebulizers, ocular drops, contact lenses, contact lens solutions, oral troches, dentifrices such as mouthwash, toothpaste, floss, periodontal treatment, etc. In each case, the composition of the present invention is administered via a vehicle whose composition is physiologically appropriate based on the area of anatomic administration.

Also based on anatomic area of involvement, the present invention may use a two or more step application process, e.g., localized application of a first composition to decrease pathological biofilms, followed by application of a second composition to promote restoration of normal commensal bacterial homeostasis.

The compositions of this invention can also be applied to inert surfaces (e.g. hospital equipment, airplane tray tables, school desks) to limit the spread/presence of pathogenic biofilms in the environment as well as in the community at large.

Another advantage of the current invention is the established safety of its components. The compositions described herein are composed of components that have already been individually established to be safe. In preferred embodiments, the compositions of the subject invention comprise a mixture of natural, generally regarded as safe (GRAS) ingredients.

Yet another advantage of the current invention is its potential to be combined with antibiotics. Since the invention has anti-biofilm effect, it makes the underlying biofilm associated infection susceptible to antibiotics typically ineffective in the biofilm treatment setting. The invention also allows antibiotics to be used at a lower amount, thereby decreasing toxicity as well as treatment expense, since the invention "sensitizes" the underlying pathogenic micro-organisms to antibiotic antimicrobial mechanism(s).

Some ingredients common to many, but not all, embodiments of the compositions of this invention include microbial metabolites, cellular and/or acellular fractions used singularly or in combination with viable or nonviable probiotic or other microbes, including bacteria, fungi and cyanobacteria such as *Arthrospira (Spirulina) platensis*, and pharmaceutical grade honey. Other ingredients that may be used in certain embodiments include, but are not limited to, prebiotic compounds such as larch or acacia gum, other hive products such as royal jelly, bee bread and propolis, green tea derivatives such as epigallocatechin gallate (EGCG) and L-theanine, other plant derivatives such as from *Inula helenium, Melaleuca alternifolia* and *Leptospermum scoparium* and water-soluble and water-insoluble Vitamin D3.

Advantageously, in preferred embodiments, ingredients of the composition of the current invention work together to inhibit biofilm-associated infections while improving associated chronic inflammatory conditions through enhancement of pathogenic biofilm dispersion as well as improvement of the normal, local innate immune response.

In the area of ocular and adnexal tissue application, the compositions of the current invention can be used for the treatment of underlying inflammatory processes associated with dry eye syndrome. The sequelae of pathogenic biofilms on or near the ocular surface can result in chronic ocular low-grade inflammatory conditions, including dry eye syndrome. The subject invention provides compositions for treating the symptoms and the causes of dry eye syndrome. Specifically, these compositions inhibit pathogenic biofilm growth and bring about an overall anti-inflammatory effect on the ocular/adnexal surface.

Such topical treatment of the ocular and adjoining surfaces improves the homeostasis between pathogenic and beneficial microflora of the ocular-adnexal area. Rebalancing or adjusting pathogenic versus nonpathogenic or even beneficial organisms improves symptoms of chronically dry, irritated, red or inflamed eyes. Such an improvement can be brought about by an embodiment of the invention comprising a topically applied mixture of live or dead microorganisms, and/or their extracts, as well as pharmaceutical grade honey that possesses anti-biofilm effect. Additionally, other compounds such as L-theanine, Vitamin D3, prebiotic polysaccharides, and the marine organism *Spirulina* can be used according to the subject invention to treat conditions associated with pathological biofilm.

The subject invention is based in part on the recognition of the role of biofilms in chronic ocular inflammatory states, specifically, dry eye syndrome. The function of the ocular and adnexal microbiome is to "boost" the local innate immune system and protect the colonized surface. Cross talk between the commensal microbial flora and ocular mucosal and immune epithelial cells helps maintain ocular surface homeostasis and ocular surface health. Commensals colonizing the ocular surface include such diverse micro-organisms as *Staphylococci, Corynebacterium, Streptococcus* and *Proprionibacterium*. This microbiome remains relatively stable unless disturbed. However, there are many common situations which are likely to affect healthy ocular and peri-ocular microbiome balance—antibiotics and other medications, contact lenses, blepharitis, meibomian gland dysfunction, ocular rosacea or other causes of chronically irritated and/or dry eyes. When normal ocular and peri-ocular micro-organism populations are disturbed by any number of possible, common causes, ocular surface irritation, inflammation and discomfort result.

Application topically applied mixture as described herein results in decreased inflammation of the ocular surface and surrounding areas. Since the many disparate causes of dry eye disease are united by the same immunopathogenesis of chronic inflammation, the invention may be used by the general public at large for symptomatic improvement of chronically dry, red, irritated and/or inflamed eyes.

Beyond treatment of dry eye, the compositions of the current invention can be used for the prevention and/or disruption of pathological biofilms and/or chronic infections present in, associated with, or leading to, various other chronic inflammatory states such as chronic rhinosinusitis; chronic periodontitis; chronic bronchitis and other states of respiratory inflammation including aspergillosis, cystic fibrosis and asthma; inflammatory otic conditions such as "swimmer's ear," otitis externa and chronic otitis; and inflammatory skin conditions such as atopic dermatitis and eczema. The pathophysiology of these conditions is likely to involve the disruption of the normal commensal bacterial population by pathogenic species and pathogenic biofilm formation. The subject invention improves symptoms associated with these conditions and the underlying inflammatory state.

DETAILED DESCRIPTION OF THE INVENTION

The subject invention provides materials and methods that effectively support innate immunity and/or disperse pathogenic biofilms using readily available, nontoxic, natural substances, while supporting restoration of normal microbiotic homeostasis.

Elements common to many but not all embodiments of the invention include a combination of one or more probiotic organisms, such as those of the genus *Lactobacillus acidophilus, Saccharomyces cerevisiae* or *Escherischia coli*, a fraction thereof and/or metabolite thereof, in combination with an anti-microbial honey with anti-biofilm effect, such as manuka honey (Medi-Honey, Comvita, New Zealand or manuka honey sterilized via ISO 11137-2a 2006 validating 15 kGy radiation sterilization dose for health care products, Food Technology Service Incorporated, Mulberry, Fla.).

Other elements that may be used in other, but not necessarily all, embodiments include prebiotic compounds such as larch or acacia gum, other hive products such as royal jelly, bee bread and propolis, green tea derivatives such as epigallocatechin gallate (EGCG) and L-theanine, and other plant derivatives such as from *Inula helenium* and the manuka bush, as well as Vitamin D3.

In its most general form, the invention provides a composition comprising a mixture of active components, which may itself be added to any vehicle appropriate for the site of application.

This particular embodiment of the invention is independent of the vehicle or carrier used in its administration. For instance, such an embodiment may be used as an "ingredient," which can be added to other existing or yet-to-be developed products. One formula for this "ingredient" form of this invention includes pharmaceutical grade honey and a probiotic organism. For instance:

Formula 1: 100 B CFU lyophilized *S. thermophilus*+100 μL honey=1 B CFU/ml 100% honey
Formula 2: 250 μL 100 B CFU/ml *S. thermophilus*+500 μL honey=25 B CFU/ml 75% honey
Formula 3: 500 μL 100 B CFU/ml *S. thermophilus*+500 μL honey=50 B CFU/ml 50% honey
Formula 4: 750 μL 100 B CFU/ml *S. thermophilus*+250 μL honey=75 B CFU/ml 33% honey
Formula 5: 900 μL 100 B CFU/ml *S. thermophilus*+100 μL honey–90 B CFU/ml 10% honey
*Specific strain *S. thermophilus* ATCC BAA-250; however, other strains may be substituted.

Gamma irradiated honey such as Medi-Honey (Comvita Inc., New Zealand) or filter sterilized honey may be used undiluted or may be diluted in sterile normal saline solution to varying final concentrations prior to the addition of probiotic. An organism such as freeze-dried *S. thermophilus* (NCFB 2393 or LMG 18311 or ATCC BAA-250) may be used and added to 100% honey or the honey-saline solution as above to obtain a final concentration of 100 Billion CFU/ml of the mixture.

Another formula for this "ingredient" form of the invention includes an enriched source of biosurfactant of 1 mg or more derived from probiotic organism(s). The yield varies with organism strain type and culture conditions. This enriched biosurfactant fraction can be diluted in standard PBS solution for varying biosurfactant concentrations. For instance:

Formula 6: 1000 μg **S. thermophilus* biosurfactant in 1000 μL ***PBS for 1 mg/ml dilution
Formula 7: 500 μg **S. thermophilus* biosurfactant in 1000 μL ***PBS for 0.5 mg/ml dilution
Formula 8: 500 μg **S. thermophilus* biosurfactant in 250 μL ***PBS for 2 mg/ml dilution
Formula 9: 500 μg **S. thermophilus* biosurfactant in 100 μL ***PBS for 5 mg/ml dilution
Formula 10: 10 mg **S. thermophilus* biosurfactant in 1 mL ***PBS for 10 mg/ml dilution
*Embodiments of biosurfactant isolation methods are described below.
**Specific strain *S. thermophilus* ATCC BAA-250; however, other strains may be substituted.
***Honey such as Medi-Honey or anti-biofilm characterized honey may be substituted for sterile, standard solution of PBS. Either such solution may be further diluted as needed.

The compositions of the subject invention can be applied directly to the involved areas, such as human mucosal, keratinized and non-keratinized epithelial surfaces. This technique reduces or eliminates systemic toxicity, because the administration is localized (skin medicament, nasal spray, oral inhaler or nebulizer, ocular drop, oral troche, et cetera).

Additionally, based on anatomic area of involvement, the present invention may use a two or more step application process, i.e., localized application of a first formulation to decrease pathological biofilms, followed by application of a second formulation to assist in restoration of normal commensal bacterial homeostasis.

Various embodiments of the invention include ocular drops, gel, ointment, cream or other vehicle of delivery of the active compounds appropriate to area of application, periocular lotion, gel, ointment, cream or other vehicle of delivery appropriate to the area of application, intranasal aqueous or non-aqueous spray, nasal saline rinse, skin soap, lotion, cream, emollient, and solution such as meant for contact lens cleaning and maintenance or spray.

Anti-biofilm efficacy of constituents, extracts, and/or mixtures of the present invention may be assessed using the Calgary Biofilm Device, an FDA Class I approved device for the inoculation of biofilms (U.S. Pat. No. 6,599,714, herein incorporated by reference) to perform the MBEC (Minimum Biofilm Eradication Concentration) procedure or other means of assessing anti-biofilm efficacy. This may include a method described in detail below. Other anti-microbial tests that can be employed include: the agar or disk-diffusion technique, the Kirby-Bauer test and the Minimum Inhibitory Concentration (MIC). These techniques are well known to those versed in the state of the arts and will not be recounted in detail here. Protocols may be found in "Techniques in Microbiology" by John Lammert, Pearson Education, 2007, and "Microbiology Laboratory Fundamentals and Applications" by George A. Wistreich, Pearson Education, 2003, which are incorporated by reference in their entirety.

Current high-throughput anti-biofilm efficacy testing is limited to essentially one test, namely the MBEC test (see above, U.S. Pat. No. 6,599,714). This particular test has a number of limitations, including non-reusability and expense of the test plates as well as the lack of effective shear force around each individual peg upon which biofilms are supposed to grow. Without adequate shear force, strong biofilm formation is not stimulated to occur and true in vivo biofilm conditions are not likely to have been approximated.

However, microbial biofilms may be grown on relatively non-porous media, such as spheres, in a rotating-tube reactor system. This non-porous media may be represented by sterile 5 mm glass spheres. The reactor vessel may be a sterile 50 ml tube polystyrene Falcon tube or a similar column placed on a rotating shaker. The tube or column may have water-tight tops such that rotations on a mechanical rotator do not result in spillage of vessel contents (i.e., contents are secured via screw-top, rubber or cork plug). The spheres may be immobilized at one end of the tube or column by an open mesh, autoclavable plastic plug. Each tube or column may contain sufficient open space such that as the device is mechanically rotated, a flushing action is generated to provide shear force to the cellular organisms adhering to the sphere surfaces without generating vacuum or static effect upon the media within the enclosed system. Devices such as tube inlets and tube outlets circulated via filtration pumps permit media replacement and aseptic removal of individual spheres by use of sterile forceps or similar device. Circulating biological growth media may be sterilized via membrane filtration. Positive determination of adequate biofilm formation growing on spheres may be performed via various microscopic staining techniques.

The biofilm which has grown on the spheres may be tested against an array of antimicrobials placed in antimicrobial susceptibility wells. Well plates or similar devices are used to create small, standard agar lawns. This technique is well known to those well versed in the state of the art and will not be recounted in detail here. Protocols may be found in "Techniques in Microbiology" by John Lammert, Pearson Education, 2007, and "Microbiology Laboratory Fundamentals and Applications" by George A. Wistreich, Pearson Education, 2003, which are incorporated by reference in their entirety. Agar is prepared, autoclaved and aliquoted into small vessels, admixed with varying concentrations of test antimicrobials and allowed to cool. Upon solidification of the agar, circular wells are punched from the agar lawn in a size equivalent to the size of the biofilm sphere. The sphere is then placed in the well.

The plates containing the wells and biofilm-coated spheres are covered and incubated in a humidified incubator at conditions appropriate for the particular organism being studied. Degree of anti-biofilm efficacy is represented by direct visualization of bacterial growth around the particular well, i.e., the smaller the diameter of growth, the greater the anti-biofilm efficacy of that particular compound. Alternatively, degree of anti-biofilm efficacy may be measured via color change created by conversion of certain stains admixed into the agar medium to enhance visualization of biofilm growth.

Antibiofilm efficacy (Biofilm Inhibitory Concentration or BIC) can be compared directly against planktonic efficacy by performing the Minimum Inhibitory Concentration (MIC) test for the same anti-microbial compounds and micro-organisms being tested. Additionally, antibiofilm efficacy can be measured using a classification system similar to the manuka factor (Molan, Peter, "Method for the assay of antibacterial activity of honey", 2005, herein incorporated by reference), except that, in this case, what is measured is the size of complete biofilm growth inhibition (biofilm inhibitory concentration, or BIC), rather than the killing diameter ("zone of inhibition") of antimicrobial substances of compounds such as honey. This procedure will be used to develop BIC standards of individual compounds, including honey, against a range of bacteria, as well as complexes of compounds together, against bacterial groups such as gram negative bacteria, methicillin sensitive and methicillin resistant *Staphylococcus*, et cetera.

In another high-throughput variation of the invention, biofilm-coated spheres as described above may be placed directly into 96 well plates and subjected to a large battery of antimicrobial compounds and/or concentrations. Biofilms may be removed from these spheres via sonication and the resulting supernatants interpreted via both plating and spectrophotometry in a process similar to that described in the MBEC procedure (see previous reference).

During culture of any organism for use in the invention, cultures may or may not be grown to maximal plateau growth phase at which time they may be harvested for maximal biofilm production.

In certain embodiments, cellular or acellular fractions or extracts of organisms or their extracellular milieu such as a biofilm derivative itself may have particular anti-biofilm and/or anti-inflammatory efficacy that may be even more effective than the source of the fraction itself.

Biofilm Inhibitory Compositions of the Subject Invention

The ingredients of the subject invention can be prepared in a variety of forms including, but not limited to, powders, suspensions, and solutions. In addition, various ingredients, such as probiotics, can be prepared as lyophilized powders or culture supernatant and/or, where appropriate, in a concentrated form.

In certain embodiments, the therapeutic composition comprises at least one probiotic organism at a concentration (B CFU/weight of the composition) of at least about 0.001 B CFU/g, 0.005 B CFU/g, 0.01 B CFU/g, 0.05 B CFU/g, 0.1 B CFU/g, 0.5 B CFU/g, 1 B CFU/g, 5 B CFU/g, 10 B CFU/g, 50 B CFU/g, 100 B CFU/g, or 500 B CFU/g.

In certain embodiments, the therapeutic composition comprises at least one probiotic organism at a concentration (B CFU/weight of the composition) of no greater than about 0.05 B CFU/g, 0.1 B CFU/g, 0.5 B CFU/g, 1 B CFU/g, 5 B CFU/g, 10 B CFU/g, 50 B CFU/g, 100 B CFU/g, 500 B CFU/g, or 1000 B CFU/g.

In certain embodiments, the therapeutic composition comprises a probiotic microorganism at a concentration (B CFU/weight of the composition) ranging from about 0.001 B CFU/g to 100 B CFU/g, 0.1 B CFU/g to 90 B CFU/g, 5 B CFU/g to 80 B CFU/g, 10 B CFU/g to 70 B CFU/g, or 30 B CFU/g to 50 B CFU/g.

In certain embodiments, the therapeutic composition comprises an ingredient at a concentration (weight of the ingredient/weight of the composition) of at least about 1 µg/g, 5 µg/g, 10 µg/g, 20 µg/g, 50 µg/g, 0.1 mg/g, 0.5 mg/g, 1 mg/g, 5 mg/g, 10 mg/g, 50 mg/g, 100 mg/g, or 500 mg/g, wherein the ingredient is selected from the group consisting of extracts of microorganisms, chemical substituents, cellular or acellular components, and/or metabolites of probiotic microorganisms, honey, hive products, biosurfactants, prebiotics, plant extracts, and vitamin D.

In certain embodiments, the therapeutic composition comprises an ingredient at a concentration (weight of the ingredient/weight of the composition) of no greater than about 10 µg/g, 50 µg/g, 0.1 mg/g, 0.5 mg/g, 1 mg/g, 10 mg/g, 50 mg/g, 100 mg/g, or 500 mg/g, wherein the ingredient is selected from the group consisting of extracts of microorganisms, chemical substituents, cellular or acellular components, and/or metabolites of probiotic microorganisms, honey, biosurfactants, prebiotics, plant extracts, and vitamin D.

In certain embodiments, the ingredient is selected from probiotic microorganisms, chemical substituents, cellular or acellular components, and/or metabolites of probiotic microorganisms.

In one embodiment, the therapeutic composition has a pH of above 5.0, 5.5, 6.0, 6.3, 6.5, 6.7, or 7.0. In one embodiment, the therapeutic composition has a pH of below 9.0, 8.5, 8.0, 7.7, 7.5, 7.3, or 7.0.

Identifying Biofilm Inhibitory Activity

Advantageously, certain compositions of the subject invention can prevent or inhibit the formation of pathogenic biofilms. In addition, certain compositions of the subject invention can reduce, control or eliminate existing pathogenic biofilms.

The compositions of the subject invention can prevent or inhibit the formation of pathogenic biofilms, and/or reduce, control or eliminate existing pathogenic biofilms via a variety of mechanisms, including preventing, inhibiting, and/or disrupting the deposition, adhesion, and/or anchoring of biofilms or pathogenic microorganisms to biological or non-biological surfaces; preventing, inhibiting, and/or disrupting the secretion and/or release of extracellular factors such as exopolysaccharide (EPS) matrix; and/or preventing, inhibiting, and/or disrupting quorum-sensing mechanisms.

In one embodiment, the subject invention provides a method for selecting one or more ingredients for the composition of the subject invention, wherein the ingredient prevents and/or inhibits the formation of biofilm by a pathogenic microorganism of interest, wherein the method comprises the following steps:

a) providing a candidate ingredient or a mixture of candidate ingredients, wherein the candidate ingredient(s) is selected from the group consisting of microorganisms, extracts of microorganisms, chemical substituents, cellular or acellular components, metabolites of microorganisms, honey, hive products, biosurfactants, prebiotics, plant extracts, and vitamin D;

b) contacting the candidate ingredient(s) with a pathogenic microorganism of interest; and c) selecting a candidate ingredient(s) if said ingredient(s) prevents or inhibits the formation of biofilm by the pathogenic microorganism of interest.

In one embodiment, which tests for prevention of biofilm, the pathogenic microorganism of interest is in a planktonic state.

In a further embodiment, one or more candidate ingredients are incubated, at a range of concentrations and/or pH, with the pathogenic microorganism of interest to determine the optimal concentration and/or pH that prevents or inhibits biofilm formation.

In a further embodiment, the method comprises the step of determining the minimum biofilm inhibitory concentration of the selected ingredient, the selected mixture of ingredients, and/or the composition of the subject invention.

In one embodiment, the candidate ingredient is selected from the group consisting of probiotic microorganisms, extract of probiotic microorganisms, chemical substituents, cellular or acellular components, and metabolites of probiotic microorganisms.

In one embodiment, the probiotic microorganism is selected from the group consisting of *Aerococcus, E. coli, Bacillus, Enterococcus, Fusobacterium, Lactococcus, Leuconostoc, Melissacoccus, Micrococcus, Oenococcus, Sporolactobacillus, Streptococcus, Staphylococcus, Saccharomyces, Pediococcus, Peptostreptococcus, Proprionebacterium,* and *Weissella*. In another embodiment, the microorganism is selected from Table 1.

In preferred embodiments, the pathogenic microorganisms or biofilms are selected from methicillin resistant *staphylococcus aureus* (MRSA), *Staphylococcus aureus, S. epidermidis, Pseudomonas aeruginosa, Pseudomonas, Haemophilus influenza, Corynebacterium, Candida,* or *Aspergillus*.

Diagnosis and Treatment of Diseases Associated With Biofilm Infections

In one embodiment, the subject invention provides methods for prevention and/or treatment of diseases caused by, or associated with, biofilms. In one embodiment, the method comprises administering, to a subject in need of such treatment, an effective amount of a composition of the subject invention.

The term "treatment" or any grammatical variation thereof (e.g., treat, treating, and treatment etc.), as used herein, includes but is not limited to, ameliorating or alleviating a symptom of a disease or condition, reducing, suppressing, inhibiting, lessening, or affecting the progression, severity, and/or scope of a condition.

The term "prevention" or any grammatical variation thereof (e.g., prevent, preventing, and prevention etc.), as used herein, includes but is not limited to, delaying the onset of symptoms, preventing relapse to a disease, increasing latency between symptomatic episodes, or a combination thereof. Prevention, as used herein, does not require the complete absence of symptoms.

The term "effective amount," as used herein, refers to an amount that is capable of preventing, ameliorating, and/or treating a pathological condition associated with biofilm.

In one embodiment, "a subject in need of such treatment" refers to a subject who is diagnosed with a pathological condition associated with a biofilm. In a specific embodiment, the subject invention comprises diagnosing whether a subject has a biofilm infection, wherein the compositions of the subject invention are then administered to the subject who is diagnosed with biofilm infection.

Diagnosis of biofilm infections can be accomplished by clinical techniques described in, for example, U.S. Patent Application Publication No. 2010/0285496. The location of pathogenic biofilm infection can be determined by imaging techniques such as, for example, X-ray and CT scans.

In one embodiment, biofilm infection can be detected by:
a) obtaining a biological sample from a subject; and
b) measuring the presence of one or more biomarkers (e.g., proteins, mRNA) that are selectively expressed by microorganisms in a biofilm state, but not in a free-floating (planktonic) state.

Additionally, biofilm infection can be detected by measuring the presence of one or more biomarkers that are expressed in elevated levels by microorganisms in a biofilm state, as compared to levels in a free-floating (planktonic) state. In another embodiment, biofilm infection can be detected by the presence of bacterial extracellular polysaccharide (EPS) matrix, or chemicals contained in the EPS.

Further, species of pathogenic microorganisms that form biofilm can be determined by, for example, using antibodies that recognize antigens or peptides released by the pathogenic microorganisms, or using probes that recognize nucleic acid molecules of the pathogenic microorganisms.

The term "biological sample," as used herein, includes but is not limited to, a sample containing tissues, cells, and/or biological fluids isolated from a subject. Examples of biological samples include but, are not limited to, tissues, cells, biopsies, blood, lymph, serum, plasma, urine, saliva, and tears. In certain specific embodiments, the biological samples include tears, nasal fluid, and saliva.

The presence and/or level of biomarkers useful according to the subject invention can be determined by techniques known in the art, such as for example, enzyme-linked immunosorbant assays (ELISA), Western blot, Northern Blot, immunological assays, immunofluorescence, and nucleic acid hybridization techniques.

Diseases Associated with Biofilm Infection

In certain embodiments, the subject invention can be used to prevent, treat, or ameliorate diseases caused by or associated with biofilm infection including, but not limited to, dermatitis, acne, chronic bronchitis, cystic fibrosis, chronic gingivitis, chronic inflammatory bowel disease, chronic eczema, chronic non-healing wounds, chronic cystitis, and medical device related inflammation such as contact lenses. The present inventors also discovered that biofilm infection causes or is associated with diseases, such as for example, chronic blepharitis and other chronic inflammatory conditions of the ocular, peri-ocular and dermatologic epithelia such as dry eye syndrome, meibomianitis and rosacea.

In one embodiment, the subject invention can be used to prevent, treat, or ameliorate conditions in otolaryngology practice implicated by biofilms, including otitis media, chronic sinusitis, chronic tonsillitis, adenoiditis, and cochlear and middle ear implant device failures. Despite the need for improved treatment methods, prior art methods such as mechanical disruption (i.e., removal or surgical excision of the infected material) or long-term antibiotic treatment remains the treatment mainstay for chronic inflammatory states due to biofilm.

The present inventors discovered that certain ocular and peri-ocular infections result from biofilm-associated chronic inflammatory states. For example, in the ophthalmic field, the presence of biofilms has been reported on endophthalmitis after cataract surgery, on scleral buckles after retinal detachment surgery, punctal plugs, artificial nasolacrimal duct tubing and on soft contact lenses associated with keratitis. In fact, microbial contamination occurs in up to 81% of all contact lens cases, 50% of contact lenses and as 30% of all types of contact lens solutions, despite use of biocides. Infections associated with bacterial biofilm formation tend to be persistent, and the most frequently isolated organisms from biofilms are *Staphylococcus aureus, S. epidermidis*, and *Pseudomonas aeruginosa*. The ocular surfaces of dry eyes and lid margins in chronic blepharitis and contact lens wearers are colonized by significantly more bacteria and significantly more gram negative type bacteria than the typically gram positive commensal bacteria found in normal eyes.

In one embodiment, the subject invention can be used to prevent, treat, or ameliorate Chronic rhinosinusitis, another example of a chronic inflammatory state associated with pathogenic biofilm formation. Pathophysiology of chronic rhinosinusitis is likely to involve the disruption of the normal commensal bacterial population by pathogens followed by pathogenic biofilm formation. Typical resulting symptoms include nasal dripping, sinus pressure, recurrent headache, post-nasal drip and cough.

In certain embodiments, the subject invention can be used to prevent, treat, or ameliorate diseases caused by or associated with biofilm infection including, but not limited to, asthma, aspergillosis, "swimmer's ear," otitis externa, chronic otitis, atopic dermatitis, chronic rhinosinusitis, allergic rhinitis, allergic conjunctivitis, chronic bronchitis, chronic gingivitis, chronic sinusitis, and chronic periodontitis.

Therapeutic Compositions and Formulations

The subject invention also provides for therapeutic or pharmaceutical compositions comprising the ingredients of the invention in a form that can be combined with a pharmaceutically acceptable carrier. In one embodiment, the composition of the subject invention is formulated for ocular, periocular, nasal, dental, or pulmonary administration.

The term "carrier" refers to a diluent, adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The therapeutic composition, if desired, can also contain minor amounts of wetting or emulsifying agents, or pH buffering agents. These compositions can take the form of solutions, suspensions, emulsion, creams, lotions, drops, sprays, gel, oils, aerosol, powders, ointment, sustained-release formulations and the like. The composition can be formulated with traditional binders and carriers such as triglycerides. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the patient. The formulation should suit the mode of administration.

In certain embodiments, the compositions of the subject invention include one or more anti-microbial, anti-bacterial, anti-viral, anti-fungal, or anti-yeast agents.

The therapeutic or pharmaceutical compositions of the invention can be formulated as neutral or salt forms. Pharmaceutically acceptable salts include salts formed with hydrochloric, phosphoric, acetic, oxalic, and tartaric acids; and sodium, potassium, ammonium, calcium, and ferric hydroxides, etc.

The subject invention also provides for the modification of the ingredient such that it is more stable once administered to a subject, i.e., once administered it has a longer time period of effectiveness as compared to the unmodified form. Such modifications are well known to those of skill in the art, e.g., microencapsulation, etc.

Modes of Administration

In one embodiment, a composition of the subject invention is delivered, via local administration, to biological surfaces including, but not limited to, eyes, teeth, gums, ears, and skin; and non-biological surfaces such as medical devices including, but not limited to, catheters, orthopedic devices, implants, prosthetic heart valves, prosthetic joints, orthopedic implants, shunts, pacemakers and defibrillators, endotracheal tubes, hemodialysis/peritoneal dialysis devices, dental implants, and intravascular catheters.

The amount of the therapeutic or pharmaceutical composition of the invention which is effective in the treatment of a particular disease, condition or disorder will depend on the route of administration, and the seriousness of the disease, condition or disorder, and should be decided according to the judgment of the practitioner and each patient's circumstances. In general, the dosage ranges from about 0.001 mg/kg to about 3 g/kg. Such a unit dose may be administered more than once a day, e.g. two or three times a day.

The amount of active ingredient that may be combined with the carrier materials to produce a single dosage form will vary, depending on the type of the condition and the subject to be treated. In general, a therapeutic composition contains from about 5% to about 95% active ingredient (w/w). More specifically, a therapeutic composition contains from about 20% (w/w) to about 80% or about 30% to about 70% active ingredient (w/w).

Following is a detailed description of various components of the invention.

Probiotics

Probiotics are micro-organisms proving beneficial in some manner to the human body. A 2001 World Health Organization symposium on probiotic micro-organisms defined these organisms as "a living micro-organism which, when it is consumed in an appropriate amount, has a positive effect on the health of its host" (World Health Organization, Joint FAO/WHO Expert Consultation on Evaluation of Health and Nutritional Properties of Probiotics in Food Including Powder Milk with Live Lactic Acid Bacteria, October 2001). Notably, however, the probiotic organism(s) employable for use in this invention may not be living; moreover, they may, in fact, include micro-organisms or fractions thereof that would normally be considered commensal or even pathogenic to the human host.

One probiotic may be used singly or probiotics can be combined for use in the invention. They can be used in the present invention in viable or non-viable form, as a fraction or fractions of the micro-organism(s), as metabolites of the micro-organisms, inactivated, semi-inactivated or combinations thereof. Fractions of the biofilm extracellular polymeric substance (EPS), or biofilm "slime", may also be used. These various extracts (fractions, metabolites) may be cellular or acellular and can be derived from intracellular or extracellular sources. For instance, metabolites such as biosurfactants may be isolated and purified and/or may be used as is available and contained in micro-organism culture supernatants. An extract composed of an acellular fraction demonstrating biosurfactant activity may be used. Such an extract may be used at concentrations ranging from10 mcg/ml to 10 grams/ml.

As another example, these extracts may include fractions of biofilms that are created when probiotics are cultured in colonies. Such fractions may be isolated, concentrated, enriched and/or consist of spent medium. They may be harvested from planktonic cultures and/or biofilm reactors. They may be harvested at any point in the organisms' growth curves. Alternatively, they may be taken at certain maximal or minimal activity phases of certain enzymes, end-products, etc.

It is well established that probiotics and other microbes/organisms can be cultured in colonies by methods including but not limited to: trickle flow/wet-dry reactors, high flow reactors, fixed bed reactors, expanded bed reactors, fluidized bed reactors, membrane reactors and spinning disk reactors. See, for example, Cheng K et al, "Advances in biofilm reactors for production of value-added products", Appl Microbiol Biotechnol, 2010, 87:445-456, which is incorporated by reference in its entirety. The particular methods of doing so are well known to those skilled in the art and are readily found in the literature. See, for example, Cotter, J et al, "Characterization of a modified rotating disk reactor for the cultivation of Staphylococcus epidermis biofilm", Journal of Applied Microbiology, 2010, 109, 2105-2117; Jackson G et al, "Growing reproducible biofilm with respect to structure and cell counts", Journal of Microbiological Methods, 2001, October, 47 (1): 1-10; O'Toole, G et al, "Initiation of biofilm formation in Pseudomonas fluoroscens WCS365 proceeds via multiple, convergent signalling pathways: a genetic analysis", Molecular Microbiology, 1998, 28(3), 449-446 and Wu, J et al, "Evaluation of Different Methods for Extracting Extracellular DNA from the Biofilm Matrix", Applied and Environmental Microbiology, August 2009, p. 5390-5395; all references are herein incorporated by reference in their entirety.

It is also well known that biofilms can be fractionated by many different methods, including but not limited to the techniques of centrifugation, filtration, heating, blending, sonication, treatment with complexing agents, treatment with ion (cation) exchanger resins and sodium hydroxide (Nielsen, P H and Jahn, A, Microbial Extracellular Polymeric Substances (eds Wingender, J., Neu, T., Flemming, H. C.), p. 49-72, Springer-Heidelberg, 1999; Thomas D P et al, "Proteomics for the analysis of the Candida albicans biofilm lifestyle", Proteomics, 2006, 6(21); 5795-804, Flemming, H et al, "The biofilm matrix", Nature Reviews in Microbiology, 2010, 8(9): 623-633; all references herein incorporated by reference in their entireties).

Fractions of biofilms such as exopolysaccharides can be concentrated through precipitation with alcohols such as ethanol or acetone (Kanmani, P et al, "Production and purification of a novel exopolysaccharide from lactic acid bacterium Streptococcus phocae P180 and its functional characteristics activity in vitro", Bioresource Technology, 2011, article in press; Aguilera, A et al, "Extraction of extracellular polymeric substances from extreme acidic microbial biofilms", Appl Microbiol Biotechnol, 2008, 78(6):1079-1088; all references are herein incorporated by reference in their entirety). Such an extract could also be used as described in TABLE 6 in concentrations ranging from 1 mg/ml to 1000 mg/ml.

Specific examples of probiotics suitable for use in the present invention include non-lactic acid as well as lactic acid producing bacteria (LAB). These include the species Bacteroides, Bifidobacterium, and Lactobacillus; also, certain strains of Aerococcus, E. coli, Bacillus, Enterococcus, Fusobacterium, Lactococcus, Leuconostoc, Melissacoccus, Micrococcus, Oenococcus, Sporolactobacillus, Streptococcus, Staphylococcus, Saccharomyces, Pediococcus, Peptostreptococcus, Proprionebacterium, and Weissella. Examples of micro-organisms suitable for use in the invention have been listed and described more extensively elsewhere (see Table 1). In one instance, for example, an extract of Lactobacillus acidophilus (ATCC 4356) and/or an extract of Escherischia coli K12 (ATCC 10798) and/or Streptococcus thermophilus 4022 (such as ATCC 19258) strains may be used.

The anti-inflammatory activity of the invention is most prominent at cell concentrations ranging from 10 million to 10 billion colony-forming units (CFUs) per milliliter (mL) (and/or the amount of metabolites produced by these numbers of bacteria).

TABLE 1

EXEMPLARY PROBIOTIC ORGANISMS AND COMMERCIAL SOURCES

| Identifier | Strain | Commercial Source |
|---|---|---|
| ATCC 25527 | Bacillus coagulans | Ganeden Inc., USA |
| | Bacteroides adolescentis | CNCM I-2168 |
| | Bifidobacterium animalis | ATCC (American Tissue Type Collection, Manassas, VA) |
| ATCC 15700 | B. bifidum | ATCC |
| DPTC 001 | B. breve | Institut Rosell Inc., Montreal, Quebec, Canada |
| | B. breve R-070 | |
| ATCC 15697 | B. infantis | ATCC |
| DPTC 047 | B. infantis BBI | Chr. Hansen, Milwaukee, WI |
| DPTC 002 | B. lactis Bb12 (ATCC27536) | Chr. Hansen |
| | B. lactis NCC2818 (CNCMI-3446) | |
| ATCC 15708 | B. longum | ATCC |
| DPTC 004 | B. longum BB46 | Chr. Hansen |
| DPTC 003 | B. longum BBL | Chr. Hansen |
| | B. longum NCC490 (CNCM I-2170) (a.k.a., B. longum Bb536 or Morinaga strain) | |

TABLE 1-continued

EXEMPLARY PROBIOTIC ORGANISMS AND COMMERCIAL SOURCES

| Identifier | Strain | Commercial Source |
|---|---|---|
| DPTC 036 | *B. spp.* Rolly | fermented milk, Snow Brand |
|  | *Escherischia coli* M-17 | BioBalance Inc., USA |
|  | *E.coli* K12 |  |
|  | *E. coli* Nissle |  |
| ATCC 4356 | *Lactobacillus acidophilus* | ATCC |
| ATCC 700396 | *L. acidophilus* | ATCC |
| DPTC 025 | *L. acidophilus* Mil | Mil fermented milk, Yakult, Tokyo, Japan |
| DPTC 049 | *L. acidophilus* Mil | Mil fermented milk, Yakult |
| DPTC 046 | *L. acidophilus* AS-1 | Quest International, Rochester, MN |
| DPTC 027 | *L. acidophilus* DDS-1 | Capsule supp., Natren Inc., Westlake Village, CA |
| DPTC 010 | *L. acidophilus* HP10 | Northeast Nutraceuticals, S. Boston, MA |
| DPTC 011 | *L. acidophilus* HP100 | Northeast Nutraceuticals |
| DPTC 012 | *L. acidophilus* HP101 | Northeast Nutraceuticals |
| DPTC 013 | *L. acidophilus* HP102 | Northeast Nutraceuticals |
| DPTC 014 | *L. acidophilus* HP103 | Northeast Nutraceuticals |
| DPTC 015 | *L. acidophilus* HP104 | Northeast Nutraceuticals |
| DPTC 048 | *L. acidophilus* HP15 | Northeast Nutraceuticals |
| DPTC 005 | *L. acidophilus* NCFM | Rhodia Inc., Madison, WI |
| DPTC 006 | *L. acidophilus* NCFM | North Carolina State University, Raleigh, NC |
| DPTC 007 | *L. acidophilus* PIM703 | Chr. Hansen |
| DPTC 008 | *L. acidophilus* SBT2062 | Snow Yogurt + 2, Snow Brand |
|  | *L. alimentarius* |  |
| ATCC 33620 | *L. amylovorus* | ATCC |
| ATCC 393 | *L. casei* | ATCC |
| DPTC 051 | *L. casei* DN-114 001 | Actimel Original fermented milk, Danone, Paris, France |
| DPTC 034 | *L. casei* LC10 | Rhodia |
| DPTC 035 | *L. casei* PIM661 | Chr. Hansen |
| DPTC 033 | *L. casei* Shirota | Joie fermented milk drink, Yakult |
| DPTC 030 | *L. casei* Shirota | Health drink produced by Yakult |
| ATCC 33820 | *L. crispatus* | ATCC |
| DPTC 009 | *L. crispatus* BG2FO4 | NCSU |
|  | *L. curvatus* |  |
| ATCC 11842 | *L. delbrueckii ssp. bulgaricus* | ATCC |
| DPTC 020 | *L. delbrueckii ssp. bulgaricus* 2038 | Yogurt, Meiji Milk Products Co. Ltd., Tokyo, Japan |
| DPTC 021 | *L. delbrueckii ssp. bulgaricus* 2038 | Yogurt, Meiji |
| DPTC 019 | *L. delbrueckii ssp. bulgaricus* MR120 | Rhodia |
| DPTC 022 | *L. delbrueckii ssp. bulgaricus* PIM695 | Chr. Hansen |
|  | *L. delbrueckii ssp. lactis* |  |
| DPTC 045 | *L. rhamnosus* MX1 | University of Western Ontario, London, Ontario, Canada |
| ATCC 33199 | *L. gallinarum* | ATCC |
| ATCC 33233 | *L. gasseri* | ATCC |
| DPTC 026 | *L. gasseri* ADH | NCSU |
| DPTC 016 | *L. helveticus* MR220 | Rhodia |
| DPTC 017 | *L. helveticus* NCK388 | NCSU |
| ATCC 33200 | *L. johnsonii* | ATCC |
| DPTC 028 | *L. johnsonii* 11088 (NCK 088) | NCSU |
| DPTC 029 | *L. johnsonii* La-1 | Nestle', Lausanne, Switzerland |
|  | *L. johnsonii* CNCM I-1225 |  |
| DPTC 018 | *L. lactis* San | Chr. Hansen |
| ATCC 25302 | *L. paracasei* | ATCC |
|  | *L. paracasei* Lpc-37 |  |
|  | *L. paracasei* ST11 NCC 2461 (a.k.a., CNCM I-2116) |  |
| ATCC 23272 | *L. reuteri* | ATCC |
| DPTC 037 | *L. reuteri* 1063-S | Biogaia Biologics, Stockholm, Sweden |
| DPTC 038 | *L. reuteri* 11284 | Biogaia Biologics |
| DPTC 039 | *L. reuteri* SD2112 | Biogaia Biologics |
| DPTC 040 | *L. reuteri* T-1 | Biogaia Biologics |
| ATCC 7469 | *L. rhamnosus* | ATCC |
| DPTC 042 | *L. rhamnosus* GR-1 | University of Western Ontario |
| DPTC 043 | *L. rhamnosus* R-011 | Institut Rosell |
| DPTC 044 | *L. rhamnosus* R-049 | Institut Rosell |
| ATCC 53103 | *L. rhamnosus* GG | ATCC |
|  | *Lactococcus lactis* |  |
|  | *Leuconostoc mesenteroides*, subspecies *cremoris* |  |
|  | *Proprionibacterium freudenrichii*, subspecies *shermanii* JS |  |

TABLE 1-continued

EXEMPLARY PROBIOTIC ORGANISMS AND COMMERCIAL SOURCES

| Identifier | Strain | Commercial Source |
|---|---|---|
| ATCC 10556 | *Streptococcus salivarius* | ATCC |
|  | *S. mitts* |  |
|  | *S. oralis* |  |
|  | *S. sanguis* |  |
|  | *S. thermophilus* S244 |  |
|  | *Staphylcoccus carnosus* |  |
|  | *S. xylosus* |  |
|  | *Vitreoscilla filiformis* |  |
| Yeast | Lyophilized yeast extract | Centro Ricerche YOMO, Milan |
|  | *Saccharomyces cerevisiae* | Health Sciences USA |
| ATCC 74012 | *S. boulardii* | Biocodex, Gentilly, France; ATCC |
| ATCC MYA-797 | *S. boulardii* | ATCC |
|  | *S. subtilis* |  |

Exemplary Materials and Methods Relating to Culture and Fractionation of Micro-Organisms As already discussed, the invention uses various materials and methods pertaining to bacterial and non-bacterial micro-organism and biofilm growth and harvesting. For example, filtrates from the yeast *Saccharomyces* may be obtained using protocols such as those described by Krasowska A et al, "The antagonistic effect of *Saccharomyces boulardii* on *Candida albicans* filamentation, adhesion and biofilm formation", FEMS Yeast Res ((2009) 1312-1321. Fractionation of planktonic and biofilm bacterial and non-bacterial cultures into various subcompartments such as nuclear, sub-nuclear, cytoplasmic, lysate, supernatant, spent medium, cellular membrane, biosurfactant, extracellular DNA, extracellular RNA and so on may then occur using any of the techniques previously referenced.

In particular, biosurfactants produced or yielded from micro-organisms can be obtained, isolated and enriched using a number of methods. These are described in scientific literature such as Baker S C et al, "Enrichment and purification of lipopeptide biosurfactants", Adv Exp Med Biol 2010; 672:281-288, Rivardo, F et al, "Anti-adhesion activity of two biosurfactants produced by *Bacillus* spp. prevents biofilm formation of human bacterial pathogens", Appl Microbiol Biotechnol (2009) 83:541-553, Gudina, E et al, "Isolation and functional characterization of a biosurfactant produced by *Lactobacillus paracasei*", Colloids and Surfaces B: Biointerfaces 76 (2010) 298-304, Gudina E et al, "Antimicrobial and antiadhesive properties of a biosurfactant isolated from *Lactobacillus paracasei* ssp. *Paracasei* A20", Letters in Applied Microbiology, 50 (2010) 419-424, Sarachat, T et al, "Purification and concentration of a rhamnolipid biosurfactant produced by *Pseudomonas aeruginosa* SP4 using foam fractionation", Bioresource Technology 101 (2010) 324-330 and Rivardo F et al, "Synergistic effect of lipopeptide biosurfactant with antibiotics against *Escherischia coli* CFT073 biofilm", International Journal of Antimicrobial Journal, (2011), article in press. All publications are herein incorporated by reference in their entirety.

Additionally, screening methods may be used to identify and assess biosurfactant producing micro-organisms. These techniques are readily found in the literature such as those described in Burch A et al, "Novel High-Throughput Detection Method To Assess Bacterial Surfactant Production", Applied and Environmental Microbiology, August 2010, p. 5363-5372 and Walter V et al, "Screening concepts for the isolation of biosurfactant producing micro-organisms", Adv Exp Med Biol 2010; 672:1-13. These publications are herein incorporated in their entirety by reference.

Honey and Other Hive Products

Used for centuries in the treatment of various ailments including infection, honey has been shown to have antimicrobial as well as anti-inflammatory effects (Viuda-Martos, M, "Functional Properties of honey, propolis and royal jelly", J Food Sci 2008 November; 73(9):R117-24). Reasons for these effects include a polysaccharide called methyl glyoxal, MGO, (Adams, C, "The origin of methylglyoxal in New Zealand manuka (*Leptospermum scoparium*) honey", Carbohydrate Research, 2009 May 26; 344(8):1050-1053), hydrogen peroxide activity, low pH, high osmolarity and antimicrobial peptide activity (Kwakman, P, "How honey kills bacteria", FASEB J, 2010 July; 24(7):2576-82). Certain honey has been shown to have anti-biofilm effect against a few pathogens; but there are no commercially available honey-based products indicated for the treatment, removal, or prevention of disease-related biofilms.

The present invention also provides methods of manufacture and characterization as well as the clinical use of standardized, pharmaceutical-grade honey. A very common ingredient of the invention at this time includes medical grade honey, such as Medi-Honey (Comvita Inc., New Zealand), which has been sterilized for use on wounds. As the antiseptic quality of honey varies based on time of year, pollens and nectars gathered, lot, season, etc., each batch of manuka honey has a measurement taken of its antiseptic potency called the "Unique Manuka Factor." As previously discussed, the UMF® number comes from a laboratory test for antibacterial activity, with the honey being compared against a standard reference antiseptic, phenol. For instance, UMF® 20+ would be equivalent in antiseptic potency to a 20% solution of phenol. No other honey to date has anti-microbial qualities measured this way.

However, this method of antiseptic characterization has 2 significant disadvantages—antimicrobial activity against the micro-organism to be treated is unknown, and this measurement is applicable only to manuka honey, and no other honey. All honey has anti-microbial qualities, which are very likely to be variable from type to type. If honey is to be included as part of the pharmaceutical anti-microbial armamentarium, it needs to be characterized like antibiotics are, via standardized, validated tests. For today's antibiotics, these include bacterial and fungal inhibitory concentration (MIC) tests as documented in the National Committee on Clinical Standards (NCCLS) reference manual (herein incorporated by reference). Anti-viral activity of honey may also be determined for particular viruses such as Respiratory Syncytial Virus (RSV) via certain procedures such as that described by Sudo K, "YM-53403, a unique anti-respiratory syncytial virus agent with a novel mechanism of action", J of Antiviral Research, 2005 (65): 125-131, herein incorporated as reference. Other well-accepted tests for anti-viral activity available commercially which may be used include the Oxoid M.I.C.Evaluators (Oxoid Ltd., United Kingdon), the Etest (BioMerieux, France) and similar others.

In particular, the anti-biofilm activity of honey needs to be standardized via biofilm inhibitory concentration (BIC) tests, which may be done, for example, by subjecting samples to the Minimum Biofilm Elimination Concentration (MBEC) test procedure (see U.S. Pat. No. 6,051,423 by Ceri et al, which is herein incorporated by reference).

As is done with antibiotics in MIC testing per standard NCCLS protocol, BIC tests of honey should be performed against common human pathogens such as *S. aureus, Pseudomonas*, methicillin resistant and methicillin sensitive *Staphylococcus aureus, Haemophilus influenza, Corynebacterium, Candida, Aspergillus*, etc. An alternative means of anti-biofilm efficacy testing using characterized biofilm spheres is also described herein. Due to intrinsic variability, each lot from various monofloral sources utilized in foraging by the honey bees (manuka, pine, orange, and so on) will be characterized according to the anti-microbial/anti-biofilm activity of the resultant honey.

Specific anti-microbial/anti-biofilm activity from monofloral honey will then be compared to various antibiotics, i.e., orange blossom honey versus ampicillin in terms of activity against *Staphylococcus aureus*. This is particularly important in the case of methicillin resistant *Staphylococcus aureus*. Alternatively, monofloral honey may be generated through the use of enclosed greenhouses in which one pollinating plant type is grown and honey bees are kept. Honey is then harvested from these hives, ensuring their monofloral and consistent nature.

Honey meant for medical use would then be sterilized via low-dose gamma irradiation or micro-filtration to be used as a topical equivalent for anti-microbial purposes as previously described in the present invention. Honey may be used between 10 and 90% volume/volume (hive product/invention). Various monofloral honeys could also be combined to provide better, more broad-spectrum coverage.

In reference to honey or hive products, samples are diluted in sterile, pH-neutral normal saline solution to test concentrations varying from 0.001% to 100% and used in place of the antibiotic(s) named in the protocols referenced above.

Hive products other than honey may also be used. For example, propolis and royal jelly, ranging from 1 mcg/ml to 10 mg/ml, may be used, prepared via methods described below.

During preparation of the invention, various samples comprised of probiotic extract and honey (e.g., *Lactobacillus* and manuka honey) may be processed using various methods and/or may remain unprocessed. Processing may include cell fractionation, heat treatment, ultrasonication, filtration, enzymatic treatment, gamma irradiation or other means of sterilization, micronization, biosurfactant isolation, crystallization and/or lyophilization, of extract samples showing anti-biofilm and anti-inflammatory activities.

Exemplary Materials and Methods Relating to Honey and Other Hive Products

Preparation of Various Extracts of Sterile Hive Products

During preparation of the invention, various samples comprised of hive products such as honey, propolis, royal jelly, bee bread or bee pollen may be processed using various methods and/or may remain unprocessed. Processing may include fractionation of proteins, sugars, pollens, polyphenols or other constituents via chemical means, high performance liquid chromatography, physical (filter) ultrafiltration, gel electrophoresis, heat treatment, enzymatic treatment, micronization, ultrasonication, crystallization, dehydration or lyophilization.

For instance, fractionation may be performed as described in Salazar-Olivo, L. A. et al, "Screening of biological activities present in honeybee (*Apis mellifera*) royal jelly", Toxicology in Vitro 19 (2005) 645-651; Mishima S et al, "Effects of propolis on cell growth and gene expression in HL-60 cells", J Ethnopharmacol 2005, 99:5-11; Nakajima Y et al, "Comparison of bee products based on assays of antioxidant capacities", BMC Complementary and Alternative Medicine 2009, 9:4; Santos, F. et al, "Antibacterial activity of Brazilian propolis and fractions against oral anaerobe bacteria", J Ethnopharmacol 2002, 80:1-7 and Maruyama, H et al, "Anti-inflammatory effect of bee pollen ethanol extract from *Cistus* sp. of Spanish origin on carrageenan-induced rat hind paw edema", BMC Complementary and Alternative Medicine 2010, 10:30, Yu, F et al, "Royal Jelly Proteome Comparison Between *A. mellifera ligustica* and *A. cerana cerana*", Journal of Proteome Research 2010, 9, 2207-2215 and Scarselli, R et al, "Towards royal jelly proteome", Proteomics 2005, 5, 769-776.

Biosurfactants

Biosurfactants are compounds released by microorganisms, and are generally non-toxic and biodegradable. In one embodiment, biosurfactants useful according to the subject invention are released by probiotics including non-lactic acid and lactic acid producing bacteria (LAB). In one embodiment, biosurfactants useful according to the subject invention are released by probiotics including, but not limited to, *Bacteroides, Bifidobacterium*, and *Lactobacillus*.

In additional embodiments, biosurfactants can be released by certain strains of *Aerococcus, E. coli, Bacillus, Enterococcus, Fusobacterium, Lactococcus, Leuconostoc, Melissacoccus, Micrococcus, Oenococcus, Sporolactobacillus, Streptococcus, Staphylococcus, Saccharomyces, Pediococcus, Peptostreptococcus, Proprionebacterium*, or *Weissella*. In another embodiment, biosurfactants can be released by one or more organisms listed in Table 1.

Biosurfactants useful according to the subject invention can be glycolipids or lipoproteins. In one embodiment, the biosurfactants can be glycolipids, lipopeptides, depsipeptides, phospholipids, substituted fatty acids, lipopolysaccharides, surlactin, surfactin, visconsin, spiculisporic acid, or rhamnolipids.

Prebiotics

Prebiotics are nondigestible, fibrous fructo- or galacto-oligosaccharides (FOS or GOS) found in many plants that are metabolized by the large intestine to form short chain fatty acids such as butyrate. These fatty acids metabolically support probiotic colonies in the intestine, as well as help generate an effective local innate immune response. Consequently, prebiotic supplementation may increase efficacy of probiotic supplementation. This combination is known as synbiotic therapy.

In certain embodiments, the invention may make use of certain prebiotics, such as locust-bean (carob) gum, in the concentration between 10 mcg-100 mg per milliliter, to augment anti-biofilm efficacy. These include fructo-oligosaccharides (FOS), manno-ologosaccharides (MOS), galacto-oligosaccharrides (GOS), arabinogalactans and other dietary fibers, inulin, lactulose, resistant starch, isomalt, oat bran, and pectin. Larch arabinogalactan may be used and is also known as AG, Ara-6, Arabinogalactan, Arabinogalactin, dietary fiber, larch, larch gum, larch tree, larix, Mongolian Larch, Mongolian Larchwood, Soluble fiber, Stractan, Western Larch, Western Larch Arabinogalactan, Wood Gum, Wood Sugar, Larix decidua, Larix europaea, Pinus Larix, Larix occidentalis, Larix gmelinii var. gmerlinii, Larix dahurica, and Abies gmelinii. Also may be used: konjac glucomannan, also known as konjac gum, hydrolyzed konjac, hydrolyzed glucomannan, unhydrolyzed konjac, hydrolyzed glucomannan, Manna, Konjac, Konjac fiber, Devil's Tongue, and Elephant-Foot Yam. Also may be used: soluble or insoluble beta glucan, also known as the bran of cereal grains, plant cellulose, fungal components, mushroom components, seaweed components, curdlan, laminarin, chrysolaminarin, lentinan, Polysaccharide-K, lichenin, pleuran, xanthan and zymosan.

Plant Extracts

Plant extracts are known to have anti-inflammatory and anti-microbial properties. Plant extracts used in some embodiments of the invention include horseheal (*Inula helenium, L. Asteraceae*, elecampane), rose (*Rosa damascena L., Rosaceae*), lavender (*Lavandula angustifolia L., Labiatae*), chamomile (*Matricaria recutica L., Asteraceae*), orange (*Rutaceae*), eucalyptus (*Eucalyptus globulus L., Myrtaceae*), geranium (*Geranium robertianum L., Geraniaceae*), juniper (*Juniperus communis L., Cupressaceae*), citrus (*Citrus sinensis L., Rutaceae*), tea tree (*Melaceuca alternifolia*), manuka bush (*Leptospermum scoparium*), neem tree (*Azadirachta indica, A. Juss*), tea plant (*Camellia sinensis*) and rosemary oils (*Rosmarinus officinalis L., Lamiaceae*). Essential oil or water distillate of the above botanicals may be used. For instance, manuka oil at a concentration between 1-10% volume/volume (plant extract/invention) may be used. Plant materials, distillates and plant oils of pharmaceutical grade quality may be purchased directly from suppliers or a hydrodistillate essence may also be generated per method described below which may also be used at a concentration between 1-10% volume/volume (plant extract/invention).

Exemplary Materials and Methods Relating to Plant Extracts
Preparation Method for Plant Extract Using Clevenger Type Apparatus or Similar Techniques During preparation of the invention, plant extracts may be prepared in various ways, particularly regarding purification of their essential oils. Please refer to Clevenger, J F, "Apparatus for the determination of volatile oil", 1928; J Am Pharm Assoc, 17; 346, incorporated herein in its entirety by reference. Other techniques may be used such as those described in Vian, M et al, "Microwave hydrodiffusion and gravity, a new technique for extraction of essential oils", Journal of Chromatography A, 1190 (2008), 14-17 or Farhat, A et al, "Eco-friendly and cleaner process for isolation of essential oil using microwave energy—experimental and theoretical study", Journal of Chromatography A, 1216 (2009), 5077-5085.

Other Plant Extracts—*Camellia Sinensis* Extracts

The invention also makes use of tea (*Camellia sinensis*) derivatives. More specifically, L-theanine and/or green tea polyphenols such as epigallocatechin gallate (EGCG), each in the amounts of 10 mcg/ml to 10 mg/ml, may be used.

Alkylamine antigens are known to stimulate innate immune response. The most concentrated plant source of alkylamine antigen is an amino acid in green tea known as L-theanine (Bukowski, J et al, "Human gamma delta T cells recognize alkylamines derived from microbes, edible plants and tea:implications for innate immunity", 1999, Immunity, Vol. 11, 57-65). L-theanine is represented by the chemical formula C2H5NHCOCH2CH2CH(NH2)COOH, D- and or L,D-theanine, 2-Amino-4-(ethylcarbamoyl)butyric acid, N-ethyl-L-glutamine, gamma-glutamylethylamide, N-gamma-Ethyl-L-glutamine, gamma-ethylamino-L-glutaminic acid, Suntheanine, 5-N-ethylglutamine, green or other tea extract, raw or refined tea leaves, roots or other components of *Camellia sinensis* or certain other *Camellia* species (i.e., *C. japonica, C. sasanqua*) or particular species of mushroom (i.e., *Xerocomus badius*).

Some tea polyphenols are known to have anti-oxidant and anti-microbial effects. Epigallocatechin gallate (EGCG) is the main polyphenol component of green tea. Other polyphenols include epigallocatechin, epicatechin gallate and epicatechin.

Vitamin D

Vitamin D has recently-discovered effects on the innate immune system besides its well known effects on bone metabolism. Vitamin D3 induces production of anti-microbial peptides (AMPs) such as cathelicidin (LL37) on body surfaces such as the skin and eye.

Vitamin D3 may be added to the formulation as an additional active ingredient. More specifically, the active form of Vitamin D may be used in an amount ranging from 1 mcg to 1 mg/ml. Yet more specifically, a form of water soluble Vitamin D currently under patent protection may be used.

Other Viable and Nonviable Organisms

Other viable or nonviable microorganisms which may be used include those that can be administered safely to humans, including human commensals, certain organisms found in the environment such as marine organisms or extremophiles such as organisms found in geothermal vents or hot springs and/or their extracts or metabolites. Human commensals are non-pathogenic organisms which normally colonize the human body while causing no disease. These include certain members of the kingdoms Monera and Fungi, including the phylum Ascomycota.

Also may be used are the yeasts *Candida, Saccharomyces, Kluyveromyces, Debaromyces, Zygosaccharomyces* and *Schizosaccharomyces* as well as *Yarrowia, Torulaspora, Pichea* and the molds *Aspergillus* and *Penicillium*. Also may be used: baker's yeast cell wall or cell wall components such as zymosan (*Saccharomyces cerevisiae*) or other yeasts, fungal components or mushroom components. Also may be used: algae, fungal and bacterial extracts ranging from 10 mcg to 100 mg weight/volume (extract/invention) and/or viable or nonviable organisms ranging between 10 million to 10 billion colony-forming units (CFUs) per milliliter (mL) (and/or the amount of metabolites produced by these numbers of organisms).

Exemplary Materials and Methods Relating to Other Viable and Nonviable Microorganisms
Polysaccharide Extract Preparation from *Spirulina platensis*

During preparation of the invention, particular extracts may be prepared from other, non-bacterial organisms, including the blue-green alga, *Spirulina platensis*. In particular, methods as described in Yang, L et al, "Inhibitory effects of polysaccharide extract from *Spirulina platensis* on corneal neovascularization", Molecular Vision 2009; 15: 1951-1961 or Pugh, N et al, "Isolation of three high molecular weight polysaccharide preparations with potent immunostimulatory activity from *Spirulina platensis, Aphanizomenon flos-aqae* and *Chlorella pyrenoidosa*", Planta Med 67 (2001) 737-742 may be used.

Following are examples that illustrate procedures for practicing the invention. These examples should not be construed as limiting.

EXAMPLE 1

Specific Embodiments For ocular, Periocular and Sinonasal Use

Specific sites of administration of the compositions of the subject invention include, but are not limited to, ocular, nasal, oral and skin. Carriers useful according to the subject invention include, but are not limited to, spray, cream, ointment, lotion, gel, drop, soap or any other form appropriate to the site of administration. These compositions can be prepared using standard methods known to those skilled in the art.

Embodiments of the invention may also be applied to inert objects, for example, as cleansing agents, such as aerosol and nonaerosol sprays, washes, soaps, etc. Embodiments may be administered as a single use, or may be administered once or more in a 24 hour period.

Although the following formulations are used for illustration, other formulation types may be used. Formulations are preferably prepared under a biocontainment hood using aseptic techniques for maximum sterility. Formulations 1-10 may use Formulae 1-10 as described above as the active components. However, each individual component may also be added individually as described below. As in the above Formulae, various organisms may be substituted for any strains of the probiotic S. thermophilus.

Formulation 1—Eye Drop Solution for Symptomatic Relief of Dry, Irritated Eyes 2 ml S. thermophilus 100 Billion CFU/1 ml sterile PBS
5 ml undiluted manuka honey
3 mls sterile normal saline solution
10 mls of 20 B CFU/ml 50% honey solution In techniques well known to practitioners of the art, the preparation is aliquoted into sterile eye-drop bottles and adjusted to neutral pH. Each bottle of eye drop solution may contain a chosen volume of the formulation, for example, 10 mls in 15 ml eye-drop bottle. The eye drop bottle may be stored at, for example, 4 degrees C. throughout the life of its use.

Formulation 2—Eye Cream for the Symptomatic Relief of Dry Eyes and Irritated Eyelids 500 B CFU freeze-dried S. thermophilus
5 mls undiluted honey
45 mls cold cream base
50 mls of 10 B CFU/ml 10% honey in cold cream base The above ingredients may be mixed in a standard cold cream well known to practitioners of the art, i.e., one composed of a base of cetyl esters wax, white wax, mineral oil, sodium borate and purified water. The preparation may be stored in a sterile jar containing 20 mls of the invention. The cold cream mixture may be stored at 4 degrees C. throughout the life of its use.

Formulation 3—Nasal Solution for the Symptomatic Relief of Chronic Sino-Nasal Congestion 10 mls nonsterile or sterile manuka honey (Medi-Honey, Comvita Inc., New Zealand)
39 mls sterile normal saline solution to a final concentration of 20% v/v
1 ml 50B CFU/ml PBS freeze-dried inactivated S. thermophilus (ATCC BAA-250)
50 mls of 1 B CFU/ml 20% honey in normal saline base Solutions can be prepared with or without preservatives and/or anti-oxidants and/or viscosity enhancers. Solutions can be filtered through 0.2 micron filters (Millipore) into 15, 20 or 30-ml sterile nasal spray bottles. The nasal spray bottle was kept stored at 4 degrees C. throughout the life of its use or alternatively may be kept at room temperature for up to 30 days.

Formulation 4—Nasal Irrigation Packets for Symptomatic Relief of Chronic Sinus Congestion 500 mg dehydrated manuka honey (see above for procedure).
Freeze-dried inactivated S. thermophilus (ATCC BAA-250) 100 billion CFU/ml (using appropriate excipients, if needed) when reconstituted in 250 mls of water.
Powdered USP grade blend of sodium chloride and sodium bicarbonate producing isotonic and pH neutral solution when reconstituted in 250 mls water. Contents of one nasal rinse packet that when reconstituted in 250 mls of water by the consumer results in 375 M CFU/ml in 4 mg/ml honey solution.

The invention in this form may be packaged with a nasal rinse bottle with a volume of 250 mls. Alternatively, the packets themselves may be packaged alone.

Formulation 5—Nasal Irrigation in Concentrated Liquid Form for the Symptomatic Relief of Chronic Sino-Nasal Congestion 2.5 mls manuka honey (Medi-Honey, Comvita Inc., New Zealand)
2.0 mls sterile normal saline solution at neutral pH
0.5 ml freeze-dried inactivated S. thermophilus (ATCC BAA-250) 100 B CFU/ml in sterile PBS
5 mls of 2 B CFU/ml in 1% honey solution (final reconstitution by consumer)

Solutions may be prepared with or without preservatives and/or anti-oxidants and/or viscosity enhancers. Solutions may be filtered through 0.2 micron filters (Millipore) into sterile 10 mls disposable containers. The solutions may or may not be packaged with nasal rinse bottles of appropriate volume to reach appropriate tonicity such that final solution when mixed with 250 mls water is isotonic.

EXAMPLE 2

Specific Embodiments for Cutaneous Use

Formulation 6—Gel for Cleansing of Chronically Irritated Dry and/or Normal Skin 50 mls manuka honey, sterile or non-sterile
40 mls normal saline solution at neutral pH containing 5% methylcellulose 1500 cP, 10% v/v
10 ml freeze-dried inactivated S. thermophilus (ATCC BAA-250) 100 B CFU/ml in sterile PBS
100 mls of 10 B CFU/ml in 50% honey solution The final product may be packaged in sterile hand-pump containers with each pump dispensing 5 mls of the invention per pump cycle. This particular form may be left on the area applied and does not require washing.

Formulation 7—Liquid Soap for Cleansing of Chronically Irritated Dry and/or Normal Skin 50 mls glycerin liquid soap base
50 mls concentrated liquid form(s) of the invention (i.e., Formulation 5 above)
100 mls of 1 B CFU/ml in 0.5% honey solution Above constituents may be combined with gentle heating and stirring and poured into 100 mls hand pump bottles, cooled and packaged.

Formulation 8—Bath Additive for Cleansing of Chronically Irritated Dry and/or Normal Skin
10 grams sodium citrate
20 grams sodium bicarbonate
10 grams crystallized or dehydrated manuka honey (see above)
100 B CFU freeze-dried inactivated *S. thermophilus* (ATCC BAA-250)
5 mls essential oil of lavender
5 mls essential oil of manuka
50 gm 2 B CFU/gm 20% honey mixture May be cured with witch hazel, placed into 50 ml domed molds, allowed to harden and packaged in air-tight disposable packaging.

EXAMPLE 3

Specific Embodiments for Environmental Use

Formulation 9—Environmental Anti-Biofilm Spray for Cleansing of Inanimate Surfaces Which May be Exposed to Pathogenic Biofilm Colonization
80 mls cleansing spray vehicle in dilute alcohol or vinegar base
10 mls non sterile manuka honey
10 mls 100 B CFU/ml PBS freeze-dried inactivated *S. thermophilus* ATCC BAA-250
100 mls 10 billion CFU/ml 10% honey solution May be packaged in hand-pump room spray containers; each pump may dispense an aerosol volume equivalent to 1 ml of solution. This particular form may be left on the area applied and does not require washing.

EXAMPLE 4

Specific Embodiments for Otic Use

Formulation 10—Ear Drop for Symptomatic Relief of Chronically Irritated, Inflamed Ears
3 ml gamma irradiated, sterile manuka honey (Medi-Honey, Comvita Inc., New Zealand)
6 mls sterile glycerin
1 ml *S. thermophilus* 100 Billion CFU/1 ml sterile PBS
10 mls 10 Billion CFU/ml 30% honey solution

EXAMPLE 5

Specific Embodiments for Respiratory Use

Formulation 11—Inhalant Solution
50 mg citric acid, anhydrous
2 mls gamma irradiated, sterile manuka honey (Medi-Honey, Comvita Inc., New Zealand)
1 ml 50 Billion CFU/ml *S. thermophilus* CFU/ml sterile PBS
97 mls sterile normal saline
100 mls 500 Million CFU/ml *S. thermophilus* CFU/ml 2% honey solution

EXAMPLE 6

Specific Embodiments for Dental Use

Formulation 12—Toothpaste
15 mls xylitol
3 mg NaCl
38 gr glycerin
2 mls thymol distillate (i.e., *Monarda* genus)
20 gr manuka honey
1 ml *S. thermophilus* 100 Billion CFU/1 ml sterile PBS
80 mls *S. thermophilus* 1.25 B CFU/1 ml

EXAMPLE 7

Specific Embodiments for Periodontal Use

Formulation 13—Curettage Agent for the Treatment of Periodontitis
Lyophilized *S. thermophilus*, at final concentration of 10 B CFU/gram of vehicle.
Manuka honey, dehydrated at 120 F, powder-milled; at final concentration of 50 gr/vehicle.
Poly(esters) on polylactide (PLA), polyglycolide (PGA), polycaprolactone (PCL) or other biodegradable copolymers may be used as a delivery vehicle for this formulation intended for subgingival administration into periodontal pockets.

The above formulation may be modified so that it could be used as a coating for dental floss, incorporated into a mouthwash, gum or lozenge.

Prebiotics, plant oil(s) and other components referenced in the detailed description of the ingredients may be added to any of the formulations of the ingredients if desired, such as other organisms including but not limited to *Spirulina*, Vitamin D3, L-theanine and EGCG.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for identifying and selecting a biologically-active composition, wherein said method comprises: (1) growing a microbial biofilm within a reactor vessel, wherein the biofilm is contacted with a biological growth medium within said reactor vessel; (2) harvesting said biofilm by removing the biofilm from the reactor vessel thereby obtaining a fraction comprising biofilm cellular mass; (3) testing said fraction that comprises biofilm cellular mass for biological activity; and (4) selecting, as the biologically-active composition, a fraction that is found to have biological activity.

2. A method for preparing a biologically-active composition, wherein said method comprises: (1) growing a microbial biofilm within a reactor vessel, wherein the biofilm is contacted with a biological growth medium within said reactor vessel; (2) harvesting said biofilm by removing the biofilm from the reactor vessel thereby obtaining a fraction comprising biologically-active biofilm cellular mass; and (3) combining said fraction with an appropriate carrier to form said biologically-active composition.

3. The method, according to claim 2, wherein the biological activity is anti-microbial activity or anti-inflammatory activity.

4. The method, according to claim 2, wherein the microbial biofilm is of a probiotic microbe selected from the group consisting of *Bacteroides, Bifidobacterium*, and *Lactobacillus*.

5. The method, according to claim 4, wherein the microbe is a *Lactobacillus*.

6. The method, according to claim 2, comprising a step of separating supernatant from the biofilm cellular mass by centrifugation or filtration.

7. The method, according to claim 1, wherein the biological activity is anti-microbial activity or anti-inflammatory activity.

8. The method, according to claim 1, wherein the biofilm is of a probiotic microbe.

9. The method, according to claim 1, wherein the microbe is selected from the group consisting of *Bacteroides*, *Bifidobacterium*, and *Lactobacillus*.

10. The method, according to claim 9, wherein the microbe is a *Lactobacillus*.

11. The method, according to claim 1, comprising a step of separating supernatant from the biofilm cellular mass by centrifugation or filtration.

12. The method, according to claim 1, wherein the biofilm is grown from a biological sample obtained from a human.

13. The method, according to claim 7, wherein the biological activity is anti-microbial activity.

14. The method, according to claim 7, wherein the biological activity is anti-inflammatory activity.

15. The method, according to claim 2, wherein the biological activity is anti-microbial activity.

16. The method, according to claim 2, wherein the biological activity is anti-inflammatory activity.

17. The method, according to claim 2, wherein the composition comprises alcohol.

18. The method, according to claim 2, wherein the composition comprises a food product.

19. The method, according to claim 2, which is a cosmetic composition and the carrier is suitable for cosmetic use.

20. The method, according to claim 3, wherein the carrier is appropriate for topical administration.

\* \* \* \* \*